US012584122B2

(12) United States Patent
Tanaka

(10) Patent No.: US 12,584,122 B2
(45) Date of Patent: Mar. 24, 2026

(54) MEDICAL DEVICE FOR CULTURING BIOLOGICAL SAMPLE AND EMBEDDING BIOLOGICAL SAMPLE IN EMBEDDING MATERIAL, KIT, AND CULTURING AND EMBEDDING METHOD

(71) Applicant: TOHOKU UNIVERSITY, Sendai (JP)

(72) Inventor: Yuji Tanaka, Kofu (JP)

(73) Assignee: TOHOKU UNIVERSITY, Sendai (JP)

( * ) Notice: Subject to any disclaimer, the term of this patent is extended or adjusted under 35 U.S.C. 154(b) by 251 days.

(21) Appl. No.: 18/246,099

(22) PCT Filed: Sep. 16, 2021

(86) PCT No.: PCT/JP2021/034192
§ 371 (c)(1),
(2) Date: Mar. 21, 2023

(87) PCT Pub. No.: WO2022/065204
PCT Pub. Date: Mar. 31, 2022

(65) Prior Publication Data
US 2023/0357745 A1 Nov. 9, 2023

(30) Foreign Application Priority Data
Sep. 23, 2020 (JP) ................................ 2020-159134

(51) Int. Cl.
*C12N 11/04* (2006.01)
(52) U.S. Cl.
CPC .......... *C12N 11/04* (2013.01); *C12N 2533/52* (2013.01)

(58) Field of Classification Search
CPC ...................................................... C12N 11/04
See application file for complete search history.

(56) References Cited

U.S. PATENT DOCUMENTS

2018/0085726 A1 3/2018 Sugiura et al.

FOREIGN PATENT DOCUMENTS

| | | | | | |
|---|---|---|---|---|---|
| CA | 2376039 | A1 | * | 12/2000 | ............... A61P 7/00 |
| CA | 2646185 | C | * | 7/2019 | ........... C12M 23/24 |
| JP | 2005-137319 | A | | 6/2005 | |
| JP | 2008-301758 | A | | 12/2008 | |
| JP | 2012-100642 | A | | 5/2012 | |
| JP | 2020-010683 | A | | 1/2020 | |
| WO | 2016/158233 | A1 | | 10/2016 | |

OTHER PUBLICATIONS

International Search Report issued on Nov. 30, 2021 in corresponding application No. PCT/JP2021/034192; 7 pgs.

(Continued)

*Primary Examiner* — Elizabeth A Robinson
*Assistant Examiner* — Jonathan E Lepage
(74) *Attorney, Agent, or Firm* — Maier & Maier, PLLC

(57) ABSTRACT

A medical device that includes: a base part that has an opening part; and a holder that holds the base part on a culture plate. The base part also has a channel that is in fluid communication with the opening part. Biological samples are cultured and embedded in an embedding material at the opening part.

6 Claims, 23 Drawing Sheets

(56)                 References Cited

OTHER PUBLICATIONS

Ben M'Barek et al., "Human ESC—derived retinal epithelial cell sheets potentiate rescue of photoreceptor cell loss in rats with retinal degeneration", Sci. Transl. Med. 9, eaai7471 (2017), 13 pgs.

Kamei, Ken-ichiro et al., "3D printing of soft lithography mold for rapid production of polydimethylsiloxane-based microfluidic devices for cell stimulation with concentration gradients." Biomed Microdevices. 2015, vol. 17. No. 36, 8 pgs.

Torisawa, Yusuke, "Engineering of vascular networks using microfluidic devices for organ-on-a-chip microsystems" Drug Delivery System. 2019, vol. 34, No. 4, pp. 268-277., 10 pgs.

* cited by examiner

401

400

1

1     301     30

400

200

100

800     150

301A
303A
30A
300A 301B
30B
304B
300B

306C

305C

30C

301C

300C

340D

306D

30D

320D

310D

305D

301D

300D

330D 101a
100a
130a
120a
140a
110a 130b
100b
101b
120b
140b
110b
160b

MEDICAL DEVICE FOR CULTURING BIOLOGICAL SAMPLE AND EMBEDDING BIOLOGICAL SAMPLE IN EMBEDDING MATERIAL, KIT, AND CULTURING AND EMBEDDING METHOD

TECHNICAL FIELD

This invention relates to a medical device for culturing a biological sample and embedding the biological sample in an embedding material, a kit for the same, and a method for the same.

BACKGROUND

Age-related macular degeneration is a disease that causes vision loss due to a macula changed by damage accumulated with aging. The age-related macular degeneration is generally classified into two types: atrophic age-related macular degeneration, which is caused by atrophy of macular tissue; and exudative age-related macular degeneration, which is caused by damage to the macula due to new blood vessels below retina.

Anti-VEGF therapy using a vascular endothelial growth factor (VEGF) is known as a treatment for exudative age-related macular degeneration. The anti-VEGF therapy is a method of injecting anti-VEGF drugs, which act on new blood vessels to shrink them and improve lesions, into a vitreous body. The anti-VEGF therapy is a popular treatment method.

Recently, a treatment method of transplanting retinal pigment epithelial (RPE) cell sheets derived from human embryonic stem (ES) cells or human induced pluripotent stem (iPS) cells to patients suffering from exudative age-related macular degeneration has been studied (Non-Patent Document 1). In the treatment method disclosed in Non-Patent Document 1, RPE cells damaged by new blood vessels are removed along with the new blood vessels and transplantation of the cultured RPE cell sheets is performed. The cultured RPE cell sheets are transplanted under the retina in a folded state. In other words, the RPE cell sheets are embedded in a hydrogel such as gelatin so that it spontaneously unfolds. Hydrogel-embedded RPE cell sheets need to be thin to facilitate injection under the retina. This is true not only for the treatment of exudative age-related macular degeneration, but also for other cell sheets for transplantation.

RELATED ART DOCUMENTS

Non-Patent Documents

Non-Patent Document 1: Ben M'Barek et al, Sci. Transl. Med. 9, eaai7471 (2017)

SUMMARY

In the conventional techniques described above, the cell sheets for transplantation need to be cultured, cut out, and embedded, each of which is a process using independent and expensive equipment, requires skilled work, and has a risk of contamination of the cell sheets.

The present inventor has developed a device for implantation and a method for culturing and embedding a biological sample that can be used to continuously perform culturing the biological sample and embedding the biological sample.

The present invention is related to a medical device for culturing a biological sample and embedding the biological sample with an encapsulation material, including: a base part with an opening part; and a holder for holding the base part to a culture dish, in which the base part has a channel in fluid communication with the opening part, and in the opening part, the biological sample is cultured and embedded with the embedding material.

Since the steps of culturing and embedding biological samples can be easily and continuously performed by the medical device, hydrogel-embedded cell sheets for transplantation can be easily prepared without contamination of the biological samples and without expensive equipments or skilled labor. In addition, cultured biological samples are not wasted.

The holder may have a straight body with a through hole and a recess for accommodating at least a part of the base part at one of ends of the straight body. The through hole may be in fluid communication with the opening part. The base part may include a spacer and a spacer support configured to contact the spacer. The spacer support may have a surface configured to contact the spacer and the surface may have at least two grooves thereon. The channel may be defined by the grooves covered by the spacer. The spacer may be made of an elastic material. The medical device may include a holding jig having a size capable of being inserted into the through hole. The holding jig has at least a head and a body.

The present invention also relates to a kit including the medical device.

In addition, the present invention is also related to a method for culturing a biological sample and embedding the biological sample by using the medical device, in which the medical device includes a base part with an opening part and a holder for holding the base part to a culture dish, the method includes: a step of setting the base part and the holder in the culture dish; a step of culturing the biological sample in the opening part; a step of embedding the biological sample cultured in the opening part with an embedding material; and a step of removing the embedded biological sample.

The method may further include a step of ejecting excess embedding material by inserting a holding jig into the holder. The culture dish may be a temperature-responsive culture dish. A well of the temperature-responsive culture dish may be coated with laminin. The embedding material may be a hydrogel. In the step of the embedding, the hydrogel at flowable temperature may be filled into the opening part. In the step of the removing, the biological sample embedded on solidification temperature of the hydrogel or less may be removed. The flowable temperature of the hydrogel may be a temperature suitable for culturing the biological sample.

DETAILED DESCRIPTION

Definition

For convenience, certain terms employed in the context of the present disclosure are collected here. Unless defined otherwise, all technical and scientific terms used herein have the same meaning as commonly understood by one of the ordinary skilled in the art to which this invention belongs. The singular forms "a", "an", and "the" are used herein to include plural referents unless the context clearly dictates otherwise.

Notwithstanding that the numerical ranges and parameters setting forth the broad scope of the invention are approximations, the numerical values set forth in the specific examples are described as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art.

Hereinafter, embodiments of the present invention are illustrated in detail. The following embodiments are illustrative only and do not limit the scope of the present invention. In order to avoid redundancy, explanation for similar contents is not repeated.

Medical Device 1

Figure 1:
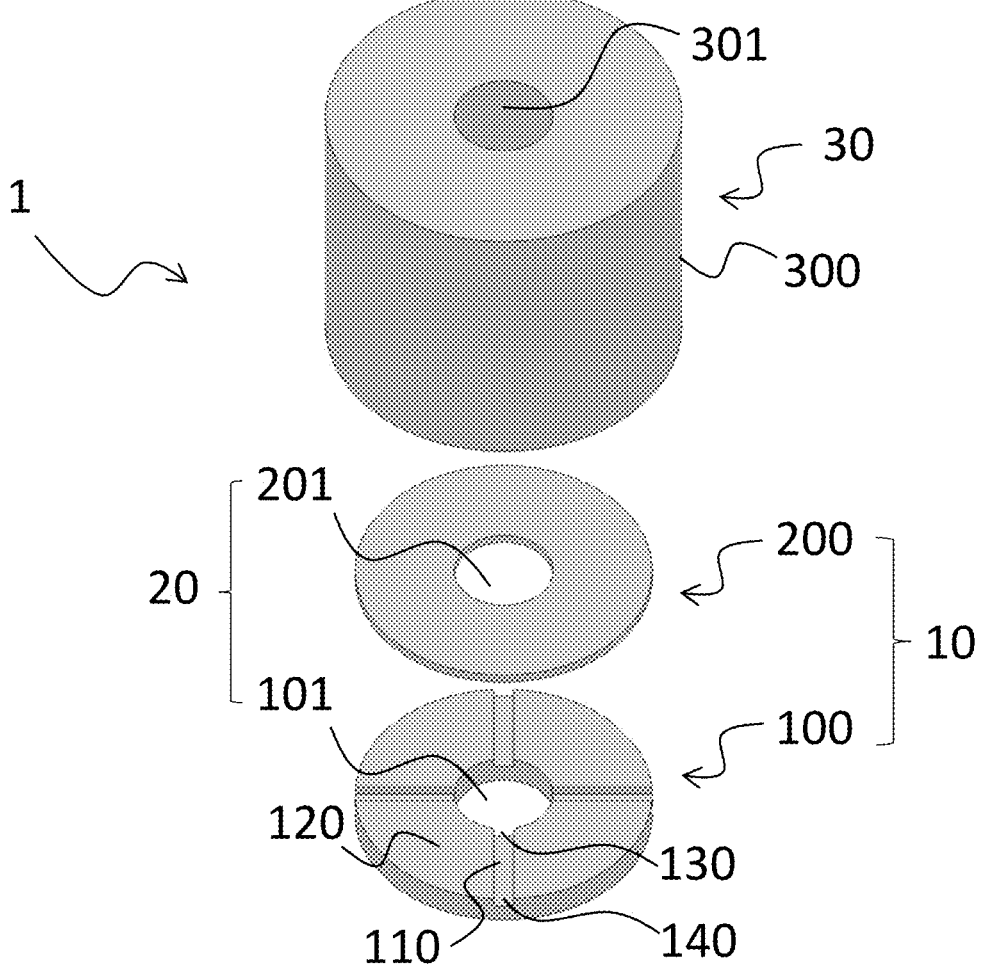
FIG. 1 shows a developed view (perspective view at front view side) of a medical device 1.

FIG. 1 shows a developed view (perspective view at front view side) of a medical device 1 according to the present embodiment. The medical device 1 according to the present embodiment has a base part 10 with an opening part 20 and a holder 30. The holder 30 is used to hold the base part 10 to a culture dish 400. The base part 10 has a channel 150 in fluid communication with the opening part 20.

The opening part 20 is a through opening. The base part 10 may include a spacer 200 and a spacer support 100 configured to contact the spacer 200. The medical device 1 may be disposable.

Spacer Support 100

The spacer support 100 has the first opening part 101. The spacer support 100 has four convex portions 120. A surface of the spacer support 100 has four grooves 110. The surface (the surface with the convex portions 120) is configured to contact the spacer 200. The groove 110 is a gap between the two convex portions 120. Each groove 110 has an inlet 130 and an outlet 140. Each groove 110 is in fluid communication with the first opening part 101 via the inlet 130 and in fluid communication with outside of the first opening part 101 via the outlet 140.

The spacer support 100 may be made of glass, metal, elastic material (e.g., silicone rubber and plastic), or a combination thereof, but preferably made of a material with high thermal conductivity to increase heating and cooling efficiency of the medical device 1 (in particular, biological sample 500 in the medical device 1) such as metal (e.g., silicon, aluminum and stainless steel).

In this embodiment, the spacer support 100 has circular shape, but may have oval shape or polygonal shape including quadrilateral shape. In this embodiment, the first opening part 101 of the spacer support 100 has circular shape, but may have oval shape or polygonal shape including quadrilateral shape. Thickness of the spacer support 100 and area of the first opening part 101 can be changed according to the biological sample 500 to be cultured.

Figure 2:
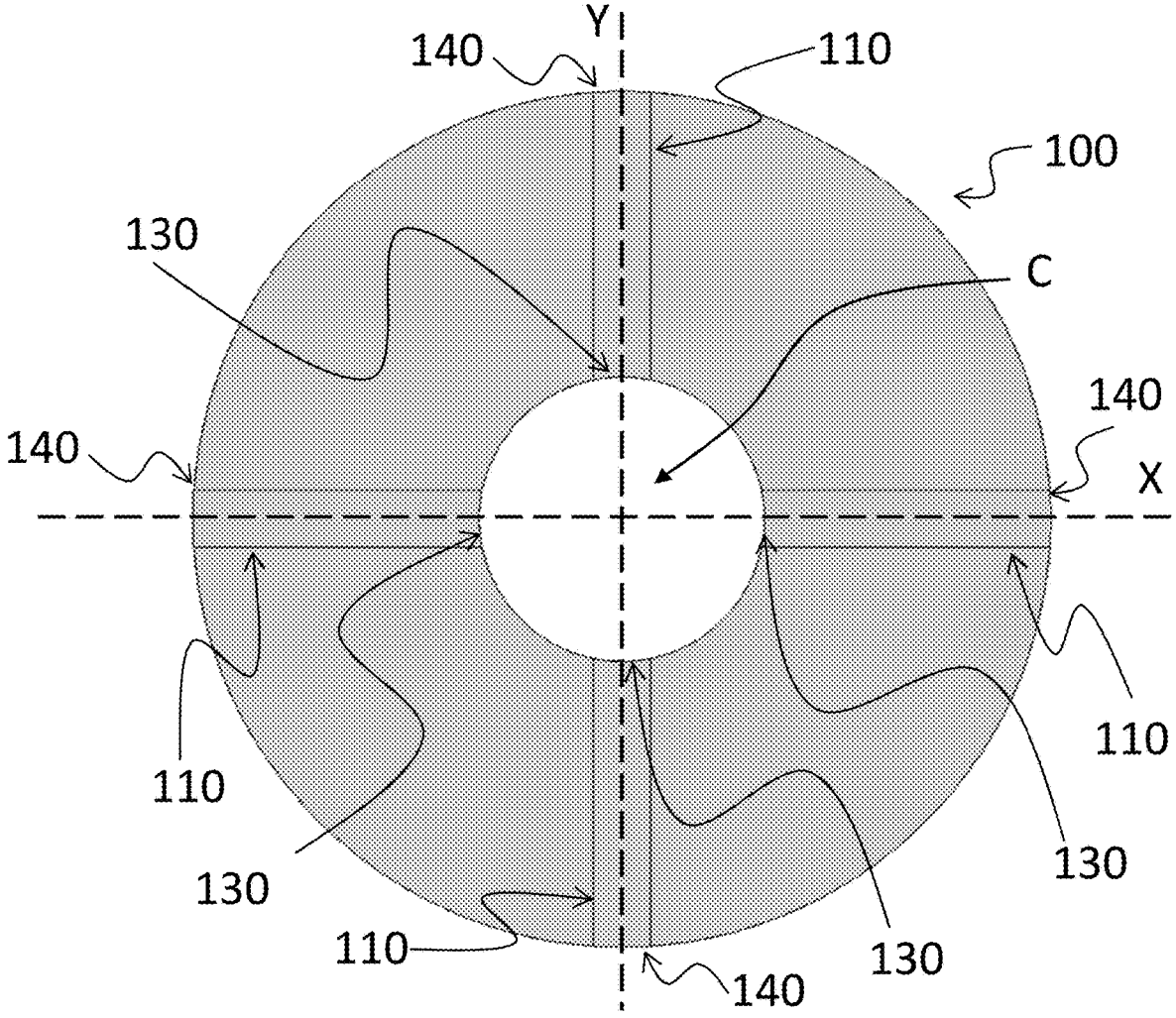
FIG. 2 shows a surface of a spacer support 100. The surface is configured to contact the spacer 200.

FIG. 2 shows the surface of the spacer support 100. The surface is configured to contact the spacer 200. For convenience of explanation, the center point C is clearly indicated at the center of the opening part 101, an auxiliary line X passing through the center point C and an auxiliary line Y orthogonal to the auxiliary line X and passing through the center point C.

In this embodiment, each of the four inlets 130 is spaced apart at equal angles with respect to the center point C. The spacer support 100 has at least one groove 110, preferably an even number of grooves 110 (e.g., 4, 6, 8, 10, and 12). Since each inlet 130 is spaced apart at equal angles with respect to the center point C, excess embedding material 700 is evenly ejected, resulting in the prevention of misalignment of the biological sample 500 within the embedding material 700.

Width and depth of each groove 110 can be changed according to type and size of the biological sample 500 and the number of grooves 110. For example, the width of each groove 110 may be within a range between two values selected from the group consisting of 1.0, 1.5, 2.0, 2.5, 3.0, 3.5, 4.0, 4.5 and 5.0 mm. The depth of each groove 110 may be within a range between two values selected from the group consisting of 0.3, 0.5, 0.7, and 1.0 mm.

Spacer 200

The spacer 200 has the second opening part 201. The second opening part 201 is in fluid communication with the first opening part 101.

The spacer 200 may be made of glass, metal, elastic materials (e.g., silicone rubber and plastic), or a combination thereof, but preferably made of elastic materials.

In this embodiment, the spacer 200 is circular shape, but may be oval shape or polygonal shape including quadrilateral shape. In this embodiment, the second opening part 201 of the spacer 200 is circular shape, but may be oval shape or polygonal shape including quadrilateral shape. Area of the second opening part 201 can be changed according to the biological sample 500 to be cultured.

Holder 30

Figure 3:
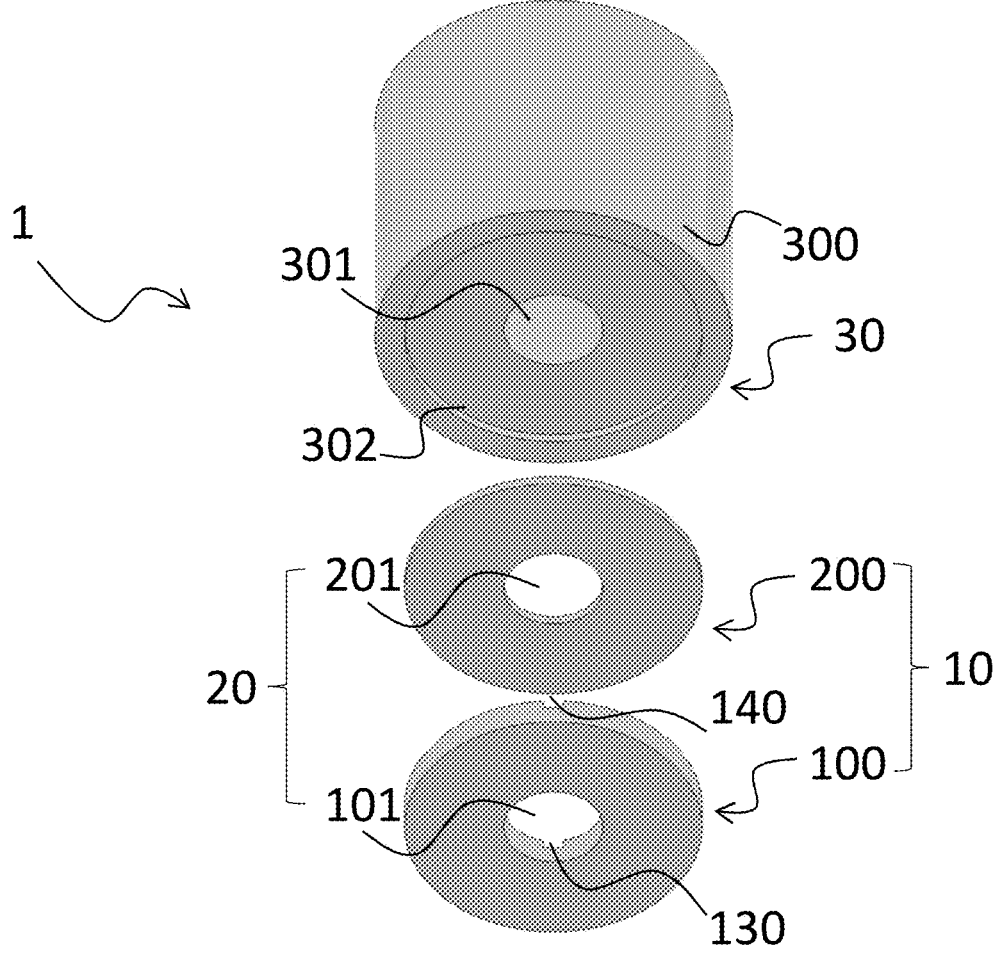
FIG. 3 shows a developed view (perspective view at bottom view side) of the medical device 1.

FIG. 3 shows a developed view (perspective view at bottom view side) of the medical device 1. The holder 30 has a straight body 300 with a through hole 301 and a recess 302 for accommodating at least a part of the base part 10 at one of ends of the straight body 300. The through hole 301 is in fluid communication with the opening part 20 (the first opening part 101 and second opening part 201). Depth of the recess 302 of the holder 30 may be the same as or shallower than the thickness of the spacer 200. Inside diameter of the recess 302 of the holder 30 may be the same as or approximately the same as outside diameter of the spacer 200, or may be larger than the outside diameter of the spacer 200. The spacer 200 may be removable from the recess 302 of the holder 30 in an engaging or screwing manner, or may be secured to the recess 302 of the holder 30 by a fixing means (e.g., adhesive).

The outer diameter of the holder 30 is larger than outer diameter of the base part 10. The outer diameter of the holder 30 preferably have a size that does not allow the medical device 1 to come off the well 401 of the culture dish 400 even if the culture dish 400 is flipped upside down with the medical device 1 set in the well 401 of the culture dish 400, but it is not limited to a size that does not allow the medical device 1 to come off the culture dish as long as the medical device 1 cannot be removed from the dish by other fixing methods. The holder 30 may be made of glass, metal, elastic material (e.g., silicone rubber and plastic), or a combination thereof, but preferably made of a material with high thermal conductivity to increase heating and cooling efficiency of the medical device 1 (in particular, the biological sample in the medical device 1) such as metal (e.g., silicone, aluminum, and stainless steel).

Assembled Medical Device 1

Figure 4:
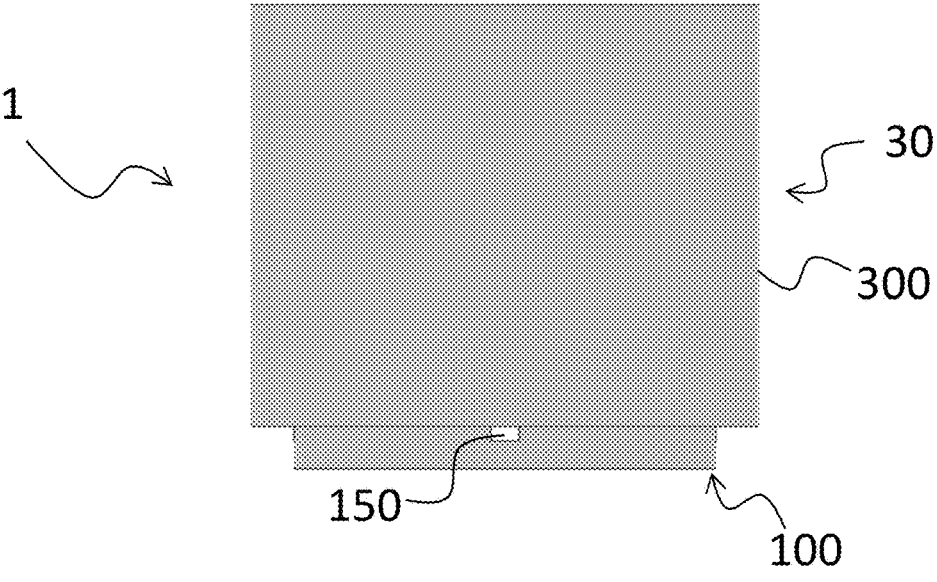
FIG. 4 shows a side view of the assembled medical device 1.
Figure 5:
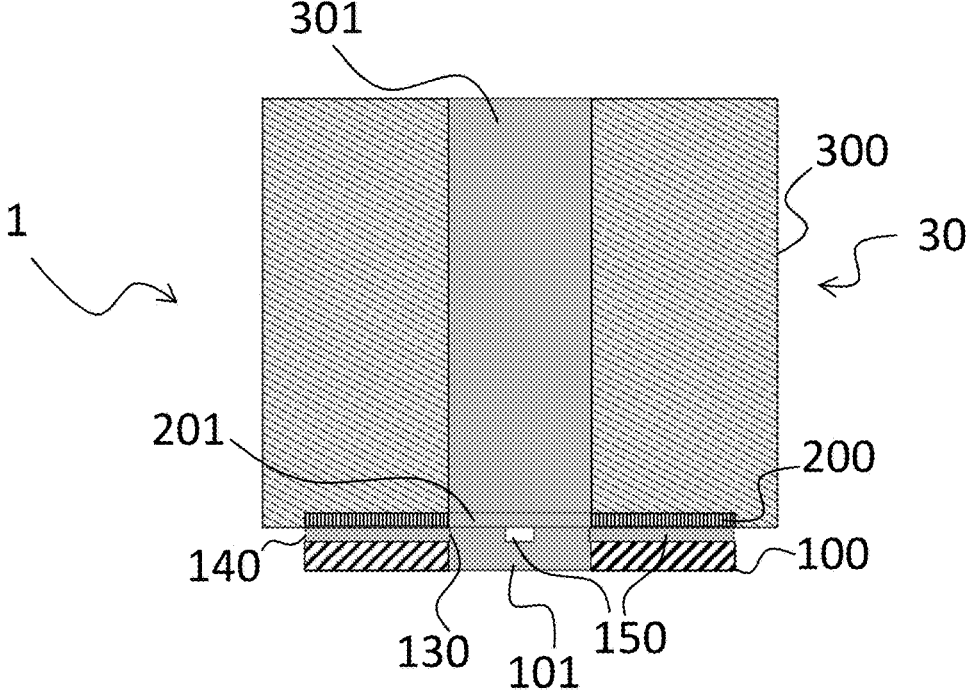
FIG. 5 shows a cross-sectional view of the assembled medical device 1.

FIG. 4 shows a side view of the assembled medical device 1, and FIG. 5 shows a cross-sectional view of the assembled medical device 1. In the assembled medical device 1, the spacer 200 is positioned between the recess 302 of the holder 30 and a surface of the spacer support 100 on a side having convex portions 120. Preferably, the channel 150 is not covered by the holder 30.

Culturing and Embedding Method

A culturing and embedding method according to this embodiment includes: a step of setting the base part 10 and the holder 30 in the culture dish 400; a step of culturing the biological sample 500 in the opening part 20; a step of embedding the biological sample 500 cultured in the opening part 20 with an embedding material 700; and a step of removing the embedded biological sample 500. In the culturing and embedding method according to this embodiment, the biological sample 500 can be cultured and the biological sample 500 can be embedded with the embedding material 700 by using the medical device 1 including the base part 10 with the opening part 20 and the holder 30 for holding the base part 10 to the culture dish 400.

1. Step of Setting Base part 10 and Holder 30 in Culture Dish 400

Figure 6:
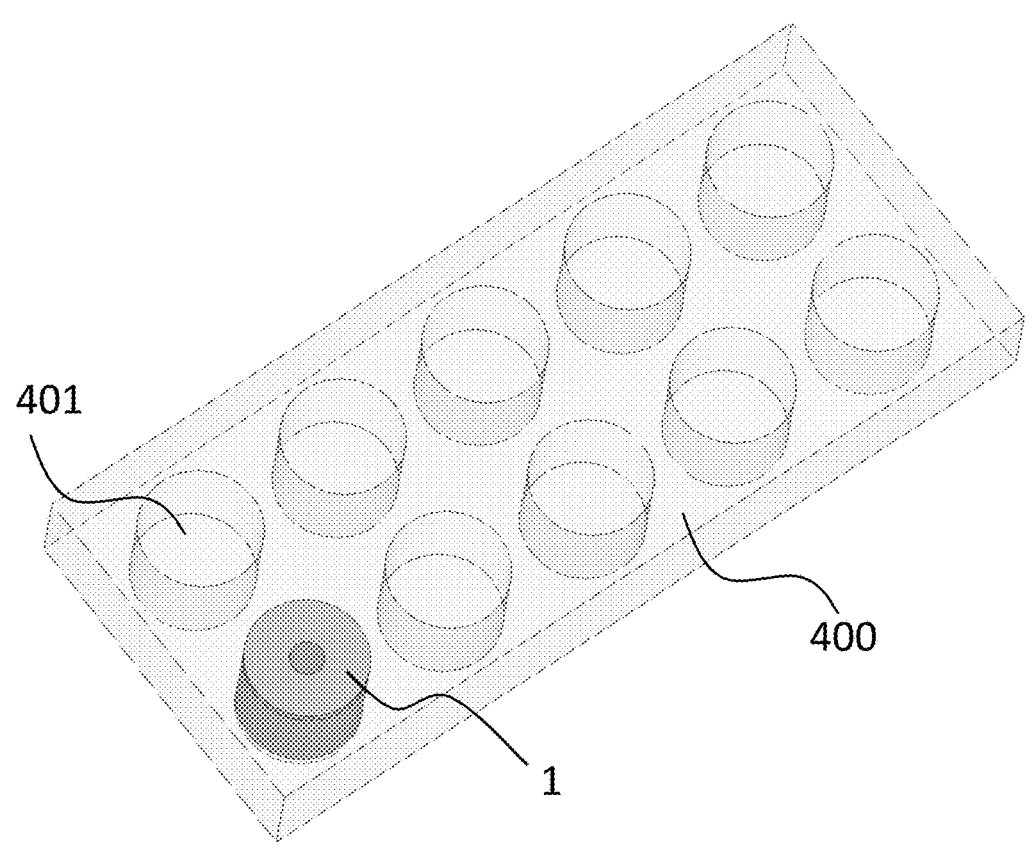
FIG. 6 shows the medical device 1 according to this embodiment which is set in one of wells 401 of a culture dish 400.
Figure 7:
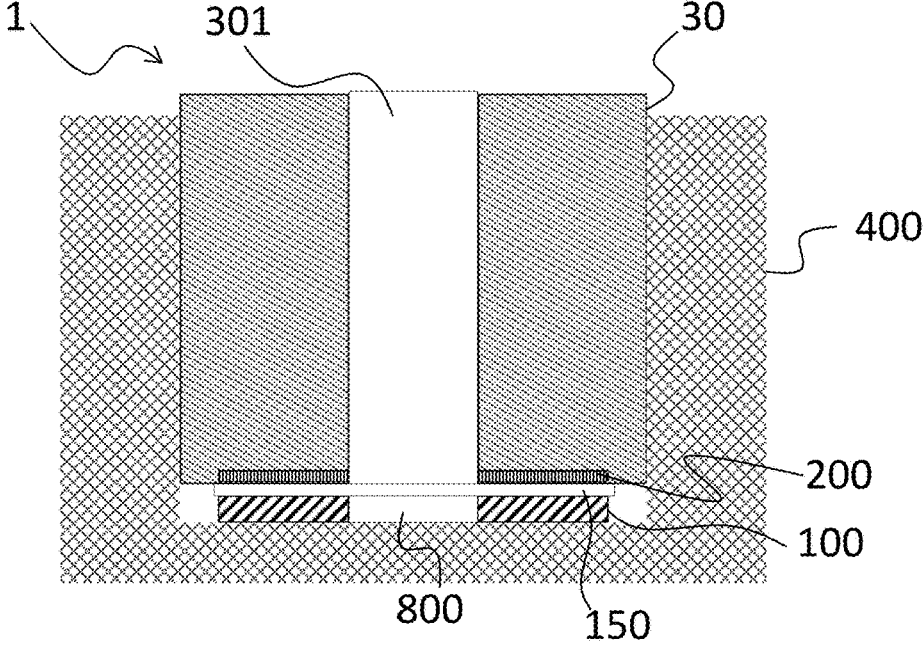
FIG. 7 shows a partial end view of the medical device 1 set in one of the wells 401 of the culture dish 400.

FIG. 6 shows the medical device 1 set in one of the wells 401 of the culture dish 400. FIG. 7 shows a partial end view of the medical device 1 set in one of the wells 401 of the culture dish 400. When the medical device 1 is set in one of the wells 401 of the culture dish 400 so that the spacer support 100 contacts a bottom of the well 401, a culture compartment 800 is defined by the first opening part 101 of the spacer support 100 and the well 401 of the culture dish 400.

The culture dish 400 is preferably a functional culture dish that allows easy detachment of a biological sample 600 from the bottom of the well 401. The functional culture dish is preferably a temperature-responsive culture dish (e.g., Upcell®, CellSeed Inc.) in which the well 401 is coated with a temperature-responsive polymer (e.g., poly-N-isopropylacrylamide (PIPAAm)) and more preferably, the temperature-responsive culture dish in which laminin is further coated on the temperature-responsive polymer coated on the wells. In the culture dish 400 in which the laminin-coated temperature-responsive polymer is coated on the bottom of the wells 401 of the culture dish 400, the biological sample adheres well to the culture dish 400, allowing it to be cultured in sheet form, and allowing the cultured sample to be more easily detached from the bottom of the wells 401. The chemical to be coated on the temperature-responsive polymer is not limited to the laminin.

2. Step of Culturing Biological Sample at Opening Part

Figure 8:
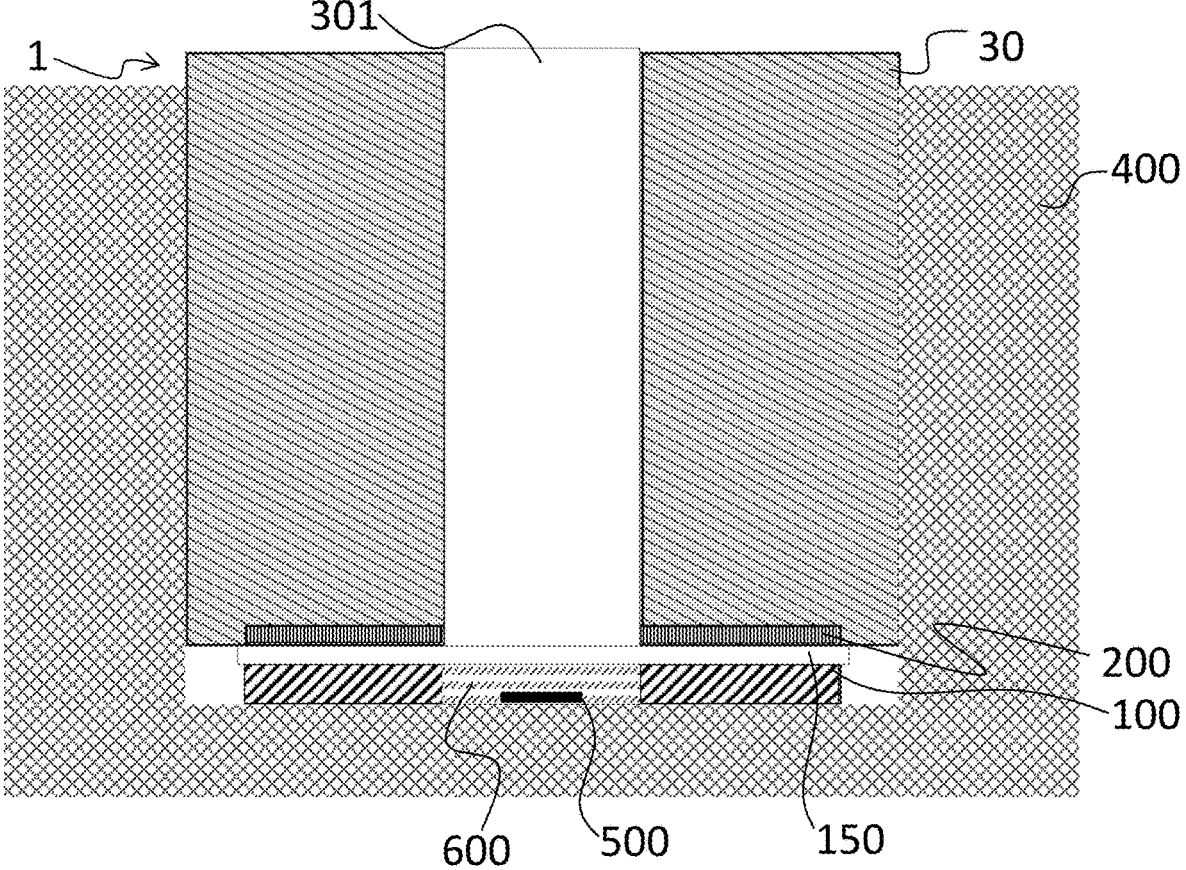
FIG. 8 shows a partial end view of the medical device 1 and culture dish 400, in which a biological sample 500 and culture medium 600 are contained in a culture compartment 800.

FIG. 8 shows a partial end view of the medical device 1 and culture dish 400, in which the biological sample 500 and culture medium 600 are contained in the culture compartment 800. The culture medium 600 and biological sample 500 are added to the culture compartment 800 through the through hole 301 of the holder 30. The biological sample 500 may be a cell sheet created by culture or a biological sample fragment, but not limited thereto. The biological sample 500 may contain a scaffold (scaffold material) such as collagen. The culture medium 600 may contain a pharmacologically effective agent (e.g., an anti-inflammatory agent or other cellular drug). Conditions (e.g., type of culture medium and temperature) in the culture process can be changed according to the biological sample 500. After the culture is completed, the culture medium 600 can be removed using a dispensing device such as a pipettor. The dispensing device can access the culture medium 600 through the through hole 301 of the holder 30. After removing the culture medium 600, the biological sample 500 can be further washed with a new culture medium 600.

Figure 9:
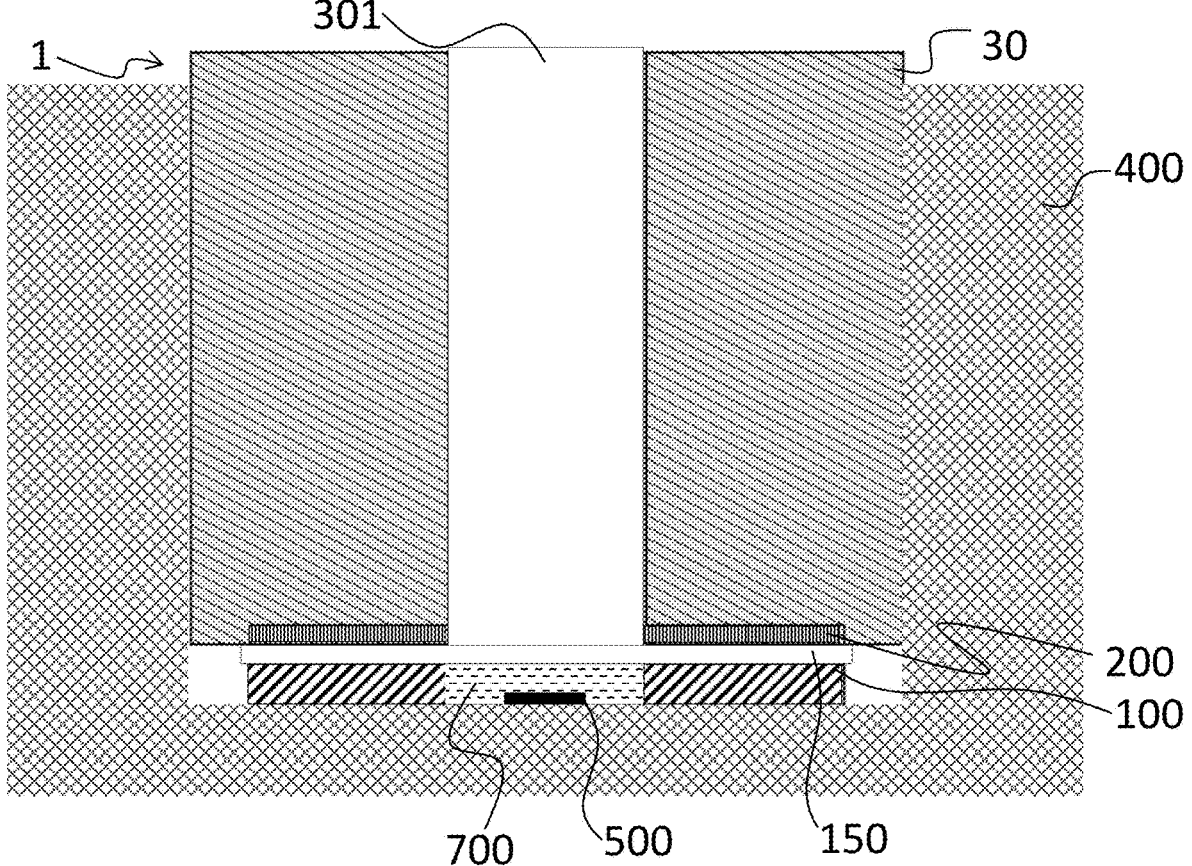
FIG. 9 shows a partial end view of the medical device 1 and culture dish 400, in which the biological sample 500 embedded in the embedding material 700 is contained in the culture compartment 800.

3. Step of Embedding Biological Sample Cultured in Opening Part with Embedding Material FIG. 9 shows a partial end view of the medical device 1 and the culture dish 400, in which the biological sample 500 embedded in the embedding material 700 is contained in the culture compartment 800. The embedding material 700 is preferably biocompatible and may be a hydrogel (e.g., gelatin, hyaluronic acid, collagen, polyacrylamide gel, collagen gel, hyaluronic acid cross-linked gel, alginate gel, thermoplastic hydrogel (such as PNIPAM polymer), and PVA gel). The embedding material 700 is filled at flowable temperature, but a temperature suitable for incubation of the biological sample 500 (e.g., 37° C.) is preferred. The embedding material 700 can be filled using a dispensing device such as a pipettor. The dispensing device can access the biological sample 500 through the through hole 301 of the holder 30.

Excess embedding material 700 is drained through the channel 150, resulting in an embedded biological sample 500 with a constant thickness. The thickness of the embedded biological sample 500 can be adjusted by the depth of the groove 100.

4. Step of Removing Embedded Biological Sample

The embedded biological sample 500 is removed at a temperature in which the embedding material 700 hardens (loses fluidity) (e.g., 4° C.) or less. The embedded biological sample 500 can be removed through the through hole 301 of the holder 30. The embedded biological sample 500 can also be removed after the holder 30, the holder 30 and spacer 200, or the medical device 1 is/are removed from the culture dish 400. If the temperature-responsive culture dish is used, the embedded biological sample 500 can be removed from the bottom of the well 401 of the culture dish 400 by heating or cooling the culture dish 400 to an appropriate temperature. If only one side of the biological sample 500 is covered with the embedding material 700, both sides of the biological sample 500 can be covered with the embedding material 700 by performing the step of the embedding described above with one side of the biological sample 500 that is covered with the embedding material 700 placed again in the culture compartment 800 so that the side is in contact with the bottom of the well 401 of the culture dish 400.

When the embedded biological sample 500 is implanted into a biological site with a syringe, for example by making it cylindrical, the shape of the biological sample 500 is restored to its original shape at the biological site due to the elasticity of the embedding material 700. The embedding material 700 is fluidized by body temperature and absorbed by a living body.

Variation of Holder 30

Figure 10:
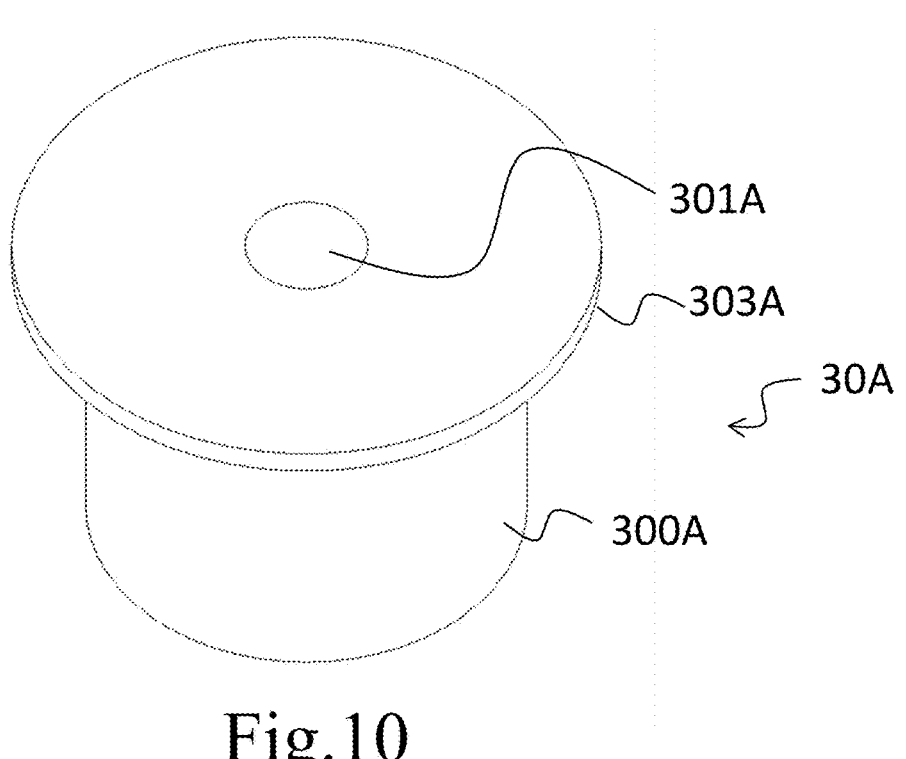
FIG. 10 shows a holder 30A according to another embodiment.

FIG. 10 shows a holder 30A according to further embodiments. The holder 30A has a straight body 300A, a recess 302 provided at one end of the straight body 300A, and a circular plate 303A provided at the other end of the straight body 300A. The straight body 300A has a through hole 301A passing through the circular plate 303A from the recess 302. Outer diameter of the circular plate 303A is larger than that of the straight body 300A. The circular plate 303A serves as a support member to assist in removing the holder 30A from the well 401 of the culture dish 400 with a finger or tool (e.g., tweezers).

Figure 11:
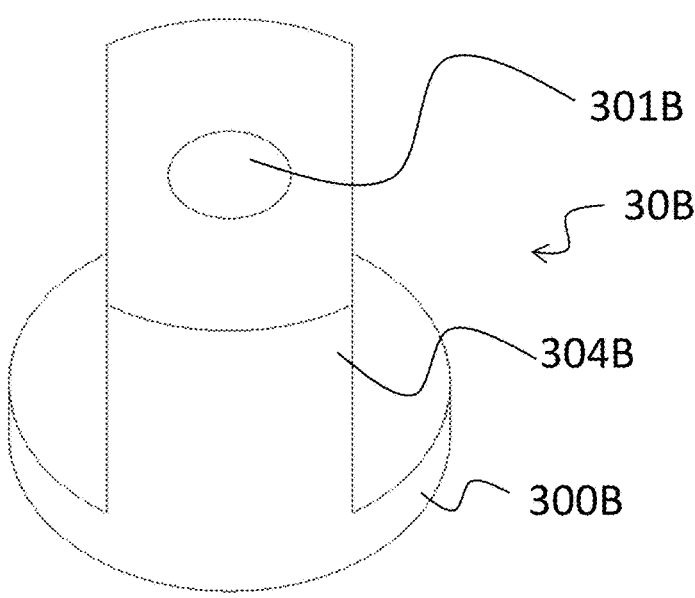
FIG. 11 shows a holder 30B according to yet another embodiment.

FIG. 11 shows a holder 30B according to still further embodiments. The holder 30B has a straight body 300B, a recess 302 provided at one end of the straight body 300B, and a protruding portion 304B extending from the other end of the straight body 300B. The straight body 300B has a through hole 301B passing through the protruding portion

304B from the recess 302. Cross-sectional area of the protruding portion 304B perpendicular to the axis of the through hole 301B is smaller than that of the straight body 300B. Two of side walls of the protruding portion 304B in FIG. 11 are configured to contact an inner wall of the well 401 of the culture dish 400. In one embodiment, only one of the side walls of the protruding portion 304B is configured to contact the inner wall of the well 401 of the culture dish 400. In another embodiment, none of the side walls of the protruding portion 304B are configured to contact the inner wall of the well 401 of the culture dish 400. Ratio of length of the protruding portion 304B to thickness of the straight body 300B can be changed. The protruding portion 304B serves as a support member to assist in removing the holder 30B from the well 401 of the culture dish 400 with a finger or tool (e.g., tweezers).

Figure 12:
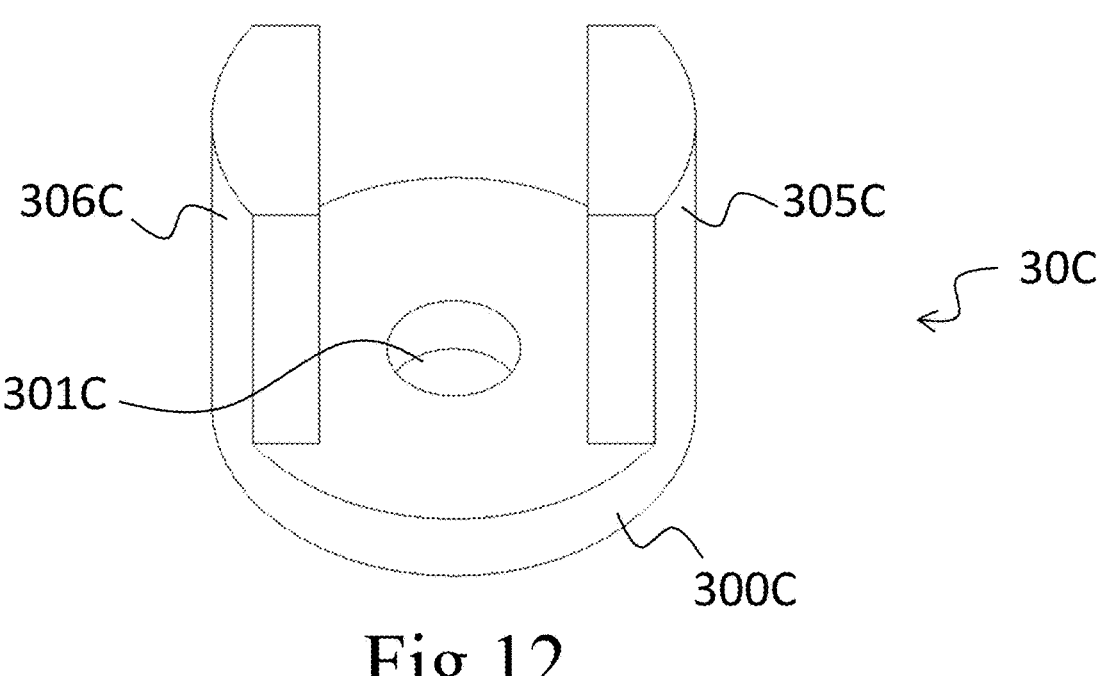
FIG. 12 shows a holder 30C according to yet another embodiment.

FIG. 12 shows a holder 30C according to still further embodiments. The holder 30C has a straight body 300B, a recess 302 provided at one end of the straight body 300C, and two arms (first arm 305C and second arm 306C) extending from the other end of the straight body 300C. The straight body 300C is provided with a through hole 301C passing through the recess 302. Both one of the side walls of the first arm 305C and one of the side walls of the second arm 306C in FIG. 12 are configured to contact the inner wall of the well 401 of the culture dish 400. In one embodiment, neither arm may be configured to contact the inner wall of well 401 of culture dish 400. Ratio of length of each arm to thickness of the straight body 300C can be changed. The length of the first arm 305C may be different from the length of the second arm 306C, but is preferably the same as the length of the second arm 306C. The first arm 305C and the second arm 306C serve as support members to assist in removing the holder 30C from the well 401 of the culture dish 400 with fingers or tools (e.g., tweezers). The holder 30C can reduce the thickness of the straight body 300C, allowing easier access to the biological sample 500 through the through hole 301C.

Figure 13:
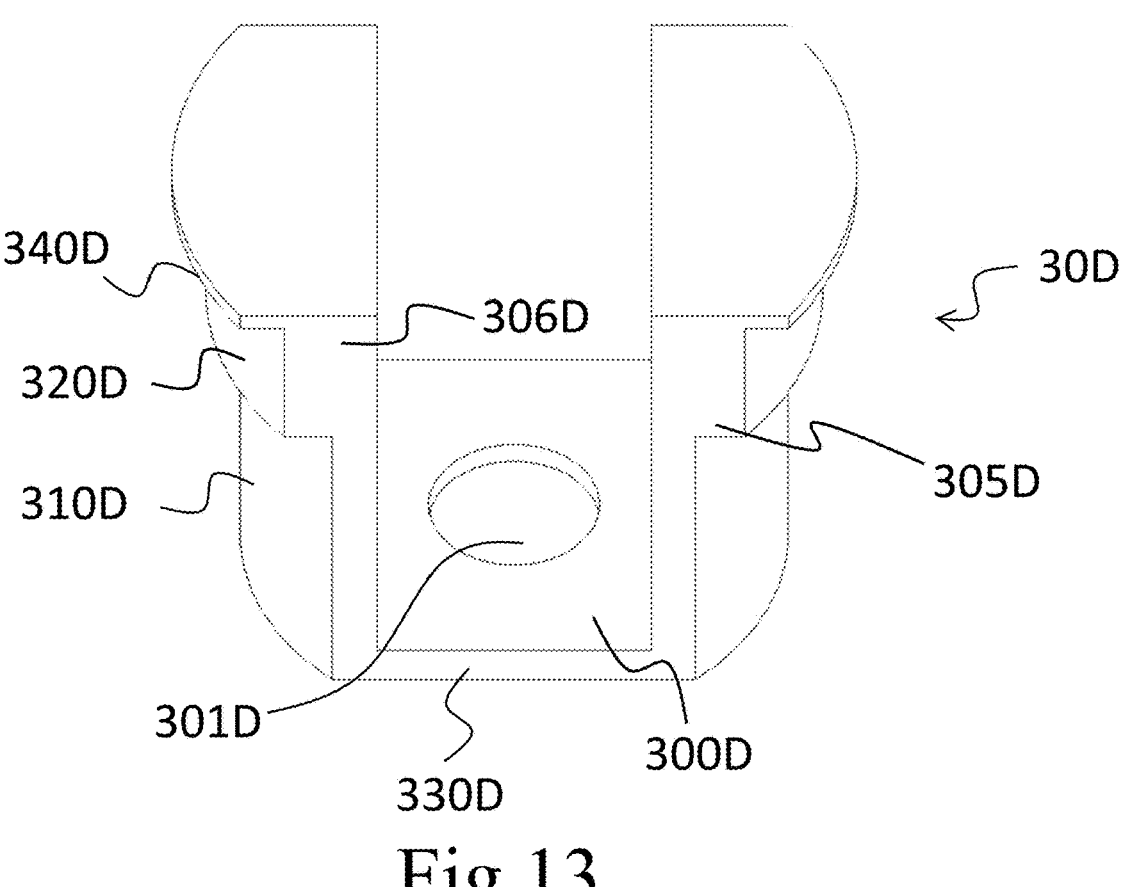
FIG. 13 shows a holder 30D according to yet another embodiment.

FIG. 13 shows a holder 30D according to still further embodiments. The holder 30D has a straight body 300D with two flat side walls 330D, a recess 302 provided at one end of the straight body 300D, two arms (first arm 305D and second arm 306D) extending from the other end of the straight body 300D, and overhangs 340D, each overhang 340D extending from one end of the respective arm. The straight body 300D has a through hole 301D through the recess 302. The two flat side walls 330D do not contact the inner wall of the well 401 of the culture dish 400. Each of the arms 305D, 306D has the first arcuate side wall 310D and the second arcuate side wall 320D. The second arcuate side wall 320D protruds more than the first arcuate side wall 310D in a direction orthogonal to the central axis of the through hole 301D. The first arcuate side wall 310D does not contact the inner wall of the well 401 of the culture dish 400. The second arcuate side wall 320D is configured to contact the inner wall of the well 401 of the culture dish 400. The longest distance from the central axis of the through hole 301D to the first arcuate side wall 310D is shorter than the shortest distance from the central axis to the second arcuate side wall 320D. The overhang 340D extends from one end of the second arcuate side wall 320D (the end opposite to the end where the first arcuate side wall 310D connects with the second arcuate side wall 320D) in a direction orthogonal to the central axis. Ratio of area of the second arcuate side wall 320D to area of the first arcuate side wall 310D can be changed as desired. By changing the area of the second arcuate side wall 320D, the force required to remove the holder 30D from the well 401 of the culture dish 400 can be changed. Length of the first arm 305D may be different from length of the second arm 306D, but is preferably the same as the length of the second arm 306D. Each of the arms 305D, 306D and each of overhangs 340D serve as support members to assist in removing the holder 30D from the well 401 of the culture dish 400 with a finger or tool (e.g., tweezers). The holder 30D can reduce thickness of the straight body 300D, allowing easier access to access the biological sample 500 through the through hole 301D. The first arm 305D and the second arm 306D may include only the second arcuate sidewall 320D without the first arcuate sidewall 310D.

Variation of Spacer Support 100

Figure 14:
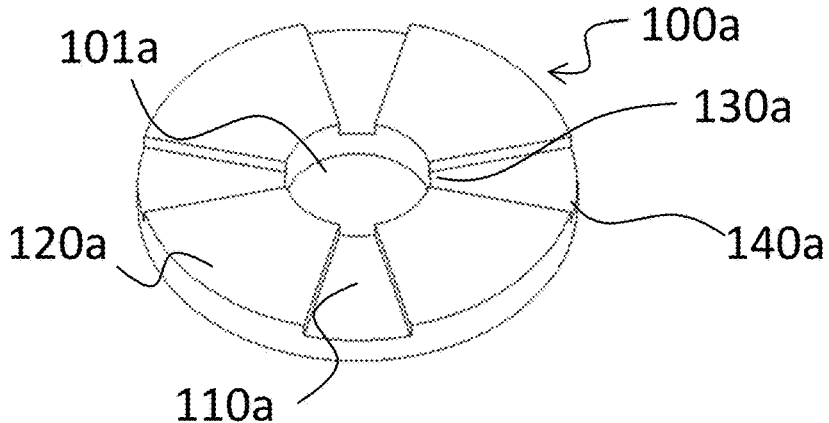
FIG. 14 shows a spacer support 100*a* according to another embodiment.

FIG. 14 shows a spacer support 100a according to still further embodiments. Width of an inlet portion 130a of the spacer support 100a is smaller than width of the corresponding outlet portion 140a (in other words, width of a groove 110a widens from the inlet portion 130a to each outlet portion 140a). The spacer support 100a can facilitate ejection of the embedding material 700 and inhibit outflow of the biological sample 500.

Figure 15:
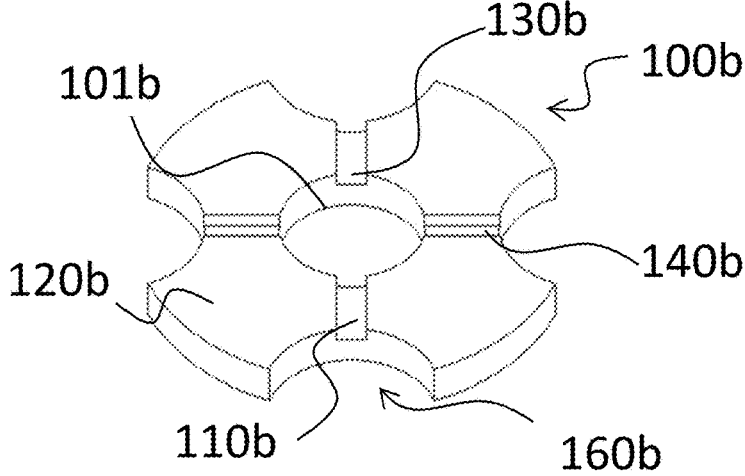
FIG. 15 shows a spacer support 100*b* according to yet another embodiment.

FIG. 15 shows a spacer support 100b according to still further embodiments. The spacer support 100b has a set of notches 160b, each notche 160b being provided on a side of an exit 140b of a groove 110b. The spacer support portion 100b allows length of the groove 110b to be shortened, thereby facilitating ejection of the embedding material 700.

Figure 16:
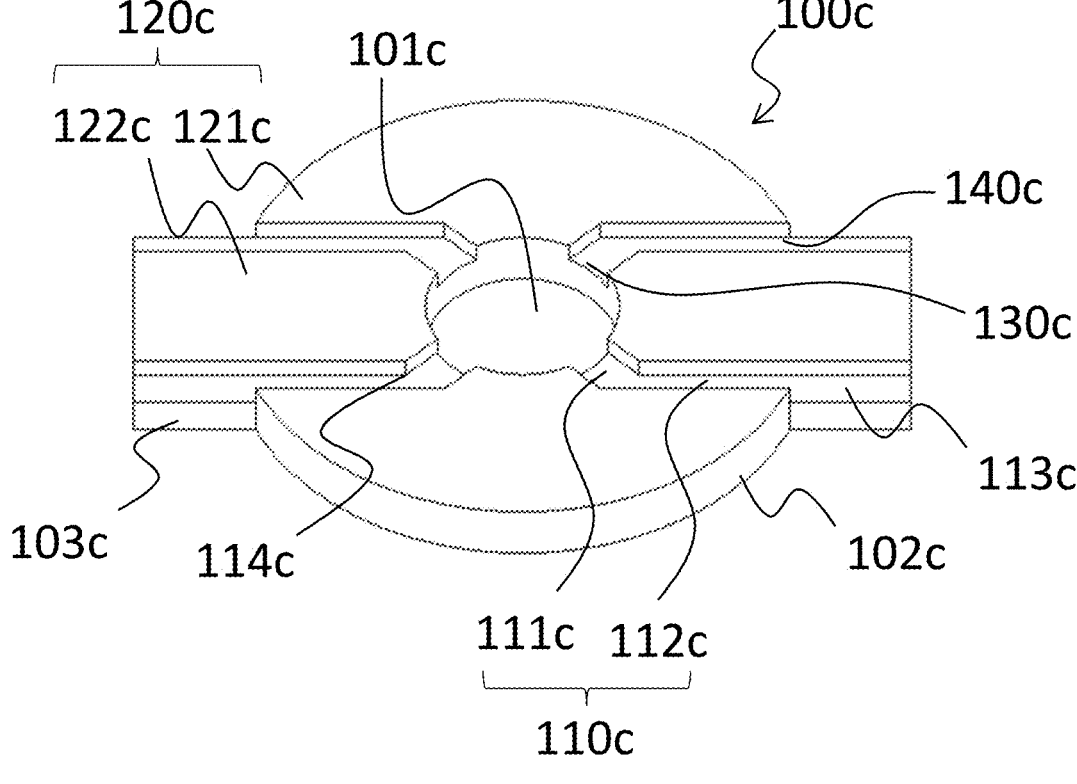
FIG. 16 shows a spacer support 100*c* according to yet another embodiment.

FIG. 16 shows a spacer support 100c according to still further embodiments. The spacer support 100c has a circular spacer support 102c with the first opening part 101c and two rectangular spacer supports 103c, each rectangular spacer support 103c extending in a direction perpendicular to the central axis of the first opening part 101c. The spacer support 100c has four grooves 110c on the surface configured to contact the spacer 200 (the surface with a convex portion 120c including two first convex portions 121c and two second convex portions 122c). Each groove 110c is a gap between the first convex portion 121c and the second convex portion 122c. Each groove 110c has an inlet portion 130c and an outlet portion 140c. Each groove 110c has a first groove 111c in fluid communication with the inlet portion 130c, a second groove 112c in fluid communication with the outlet portion 140c, and a bend 114c where the direction of fluid flow changes between the first groove 111c and the second groove 112c. Each outlet portion 140c connects to a partial groove 113c. The partial groove 113c is a groove with walls and bottom derived from the rectangular spacer support 103c and without walls derived from the circular spacer support 102c. The partial groove 113c can disperse the position of the flow out of the embedding material 700 to the bottom of the well 401 of the culture dish 400, thereby preventing clogging of the embedding material 700 at the outlet portion 140c, even when the viscosity of the embedding material 700 is high.

Medical Device 1001

Figure 17:
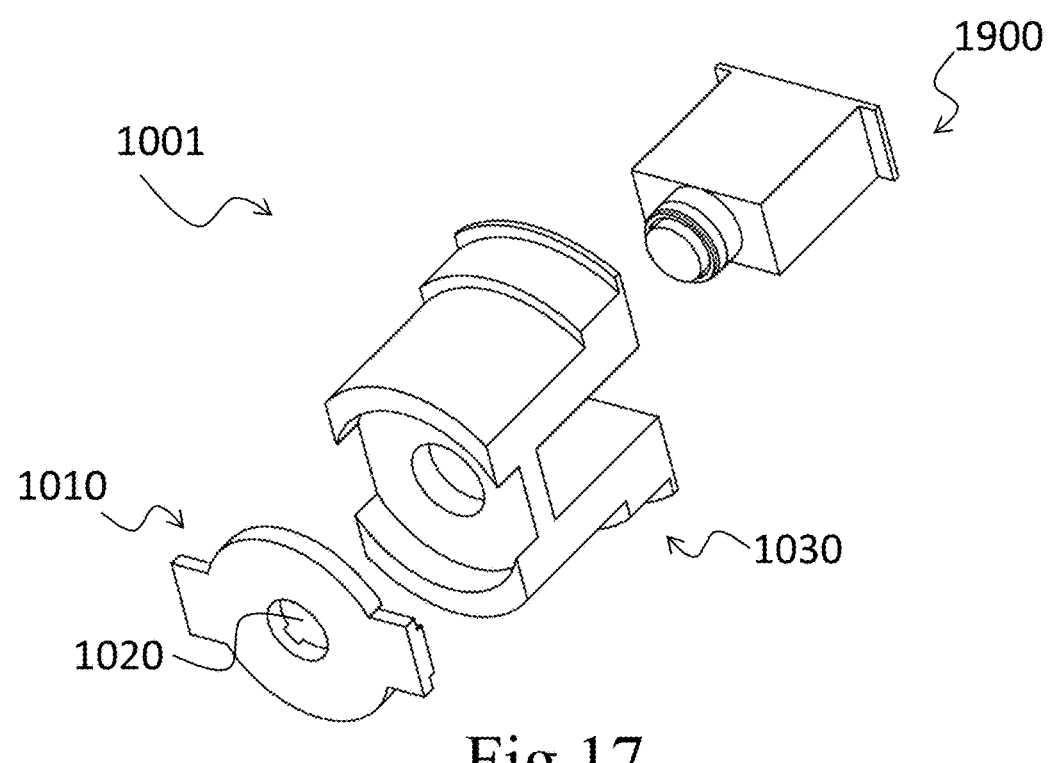
FIG. 17 shows a developed view of a medical device 1001 according to another embodiment.
Figure 18:
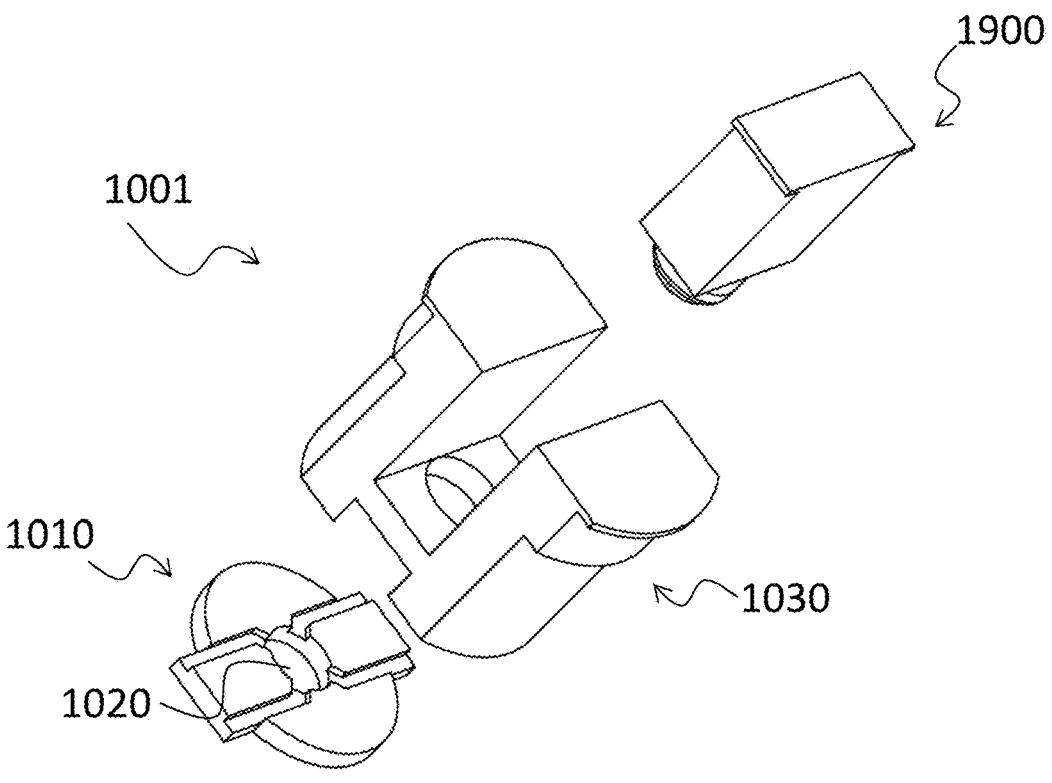
FIG. 18 shows a developed view of the medical device 1001 based on a different viewpoint from the viewpoint in FIG. 17.

Each of FIGS. 17 and 18 shows a developed view of a medical device 1001 according to further embodiments. The medical device 1001 in this embodiment has a base part 1010 with an opening part 1020, a holder 1030, and a holding jig 1900. The base part 1010 in this embodiment does not have a spacer, but may have a spacer. The base part 1010 has a structure that is generally identical to the spacer support 100c, but may be other spacer supports. In the following, only the differences between medical devices 1 and 1010 are shown.

Holder 1030

Figure 19:
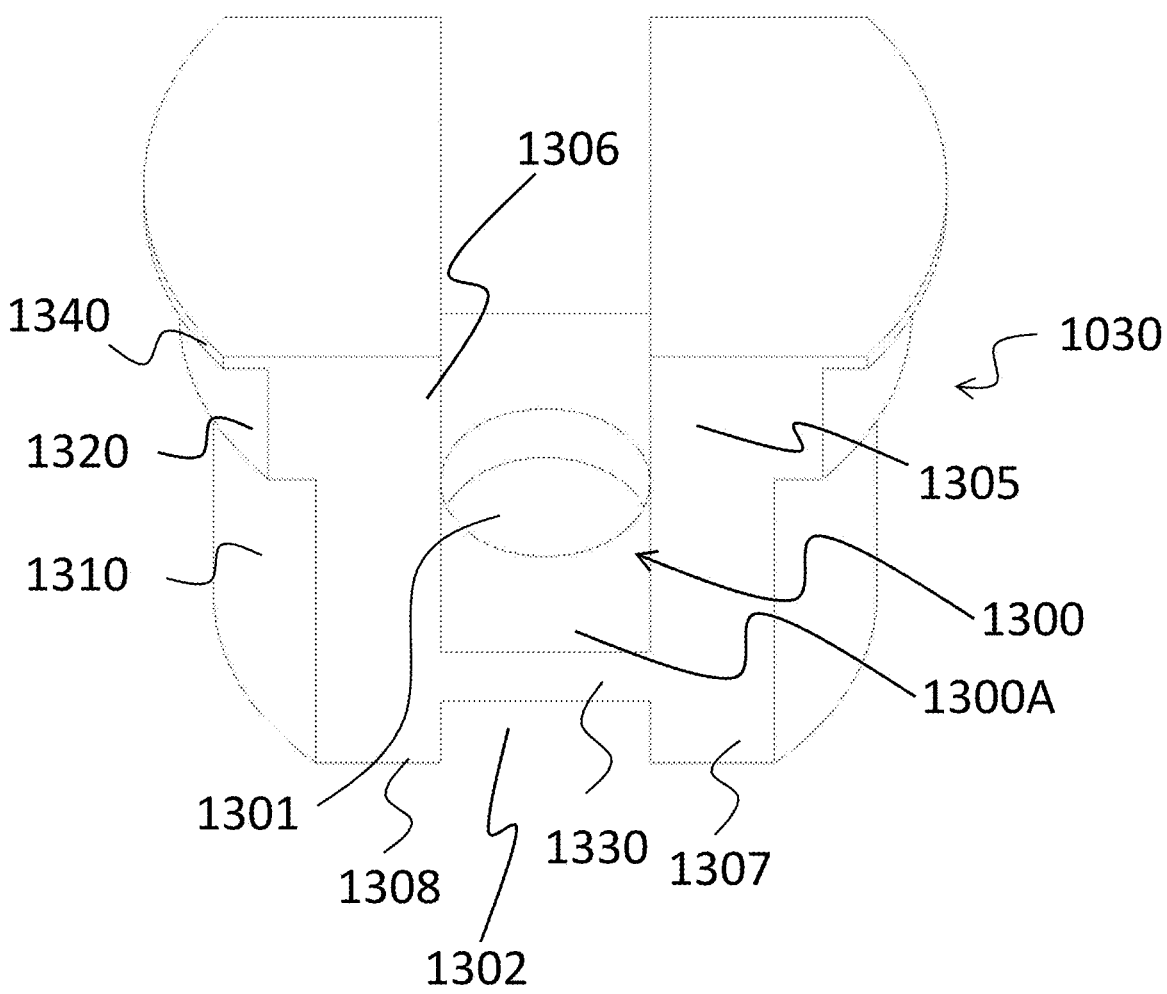
FIG. 19 shows a holder 1030 of the medical device 1001.
Figure 20:
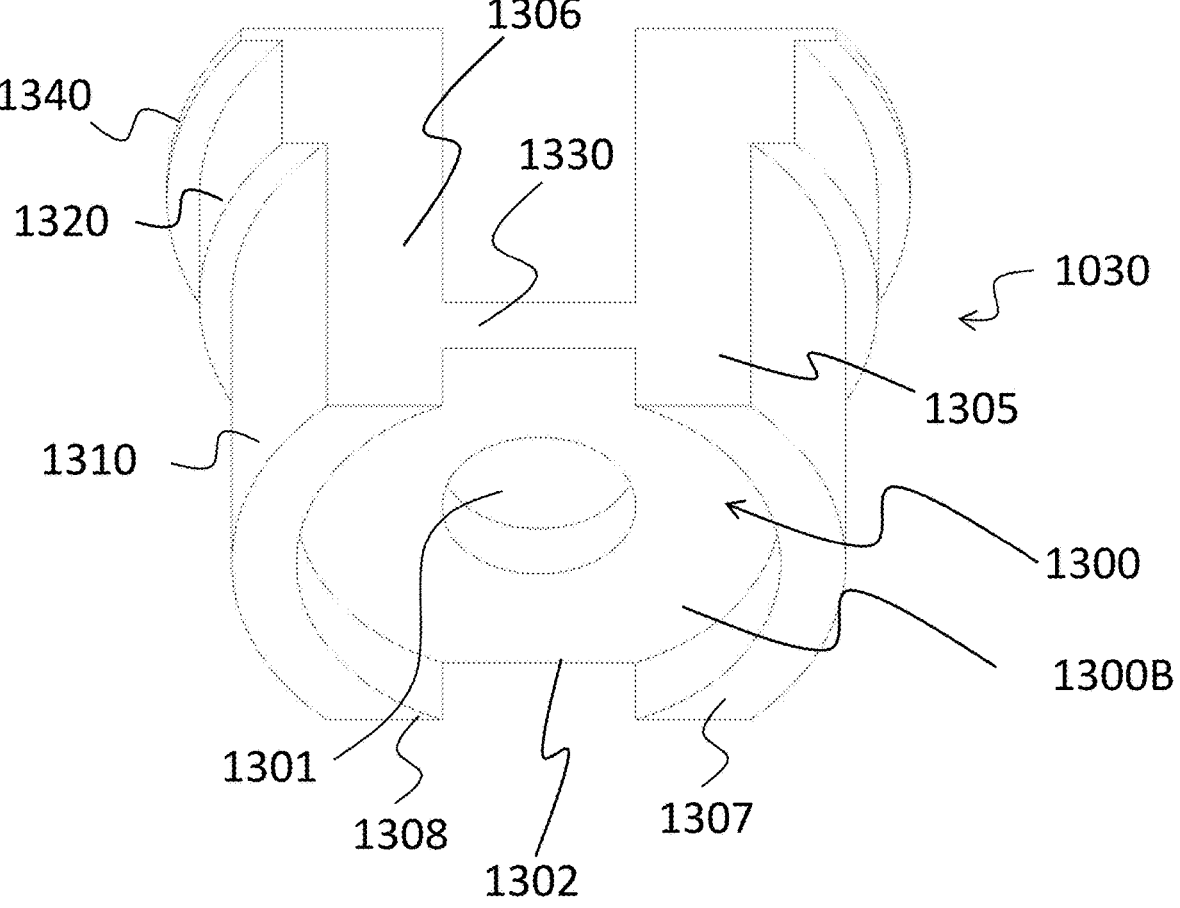
FIG. 20 shows the holder 1030 of the medical device 1001 based on a different viewpoint from the viewpoint of FIG. 19.

Each of FIGS. 19 and 20 shows a holder 1030 according to this embodiment. The holder 1030 has: (1) a straight body 1300 with two flat side walls 1330, a surface 1300A, a back surface 1300B located opposite the surface 1300A, and a through hole 1301 extending from the surface 1300A to the back surface 1300B; (2) two arms (first arm 1305 and second arm 1306), each arm extending from the surface 1300A so as to sandwich the through hole 1301; (3) overhangs 1340, each overhang 1340 extending from a tip of the respective arm orthogonally to and away from the central axis of the through hole 1301; and (4) two legs (first leg 1301 and second leg 1308), each leg extending from the back surface 1300B to sandwich the through hole 1301.

The first arm 1305 and first leg 1307 have the first arcuate side wall 1310 in common with each other. The second arm 1306 and second leg 1308 have the first arcuate side wall 1310 in common with each other. Each of the arms 1305 and 1306 further has the second arcuate side wall 1320, the second arcuate sidewall 1320 being orthogonal to the central axis of the through hole 1301 and projecting more than the first arcuate side wall 1310 in a direction away from the central axis. The holder 1030 has a recess 1302 defined by the back surface 1300B, the first leg 1307 and the second leg 1308. The recess 1302 can accommodate at least a portion of the base part 1010.

Hold Down Jig 1900

Figure 21A:
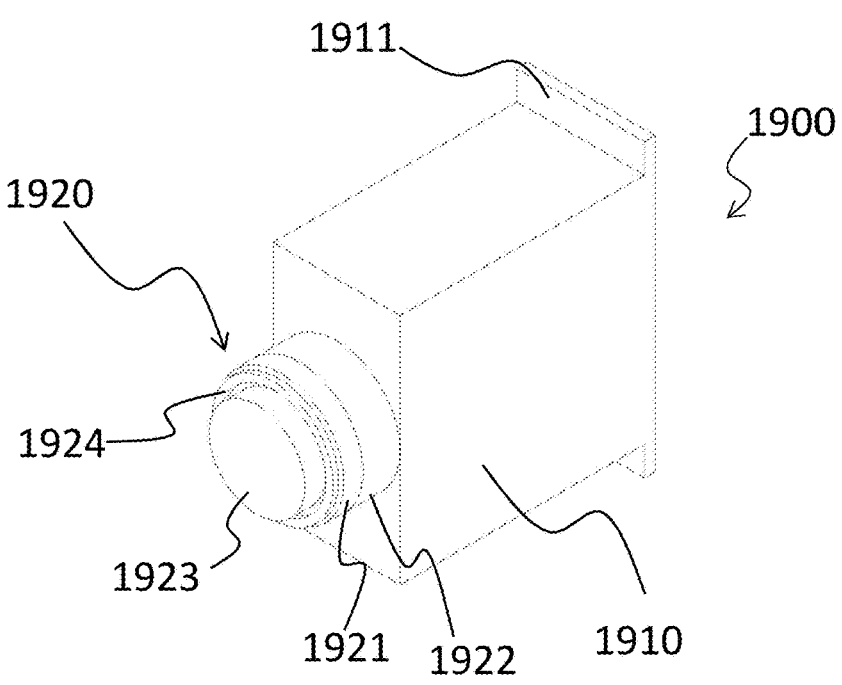
FIG. 21A shows a holding jig 1900 for the medical device 1001.

FIG. 21A shows a holding jig 1900 according to this embodiment. The holding jig 1900 has a body 1910, a head 1920 protruding from one end of the body 1910, and two protruding plates 1911, each protruding plate extending from the other end of the body 1910 orthogonal to and away from the central axis of the head 1920.

Figure 21B:
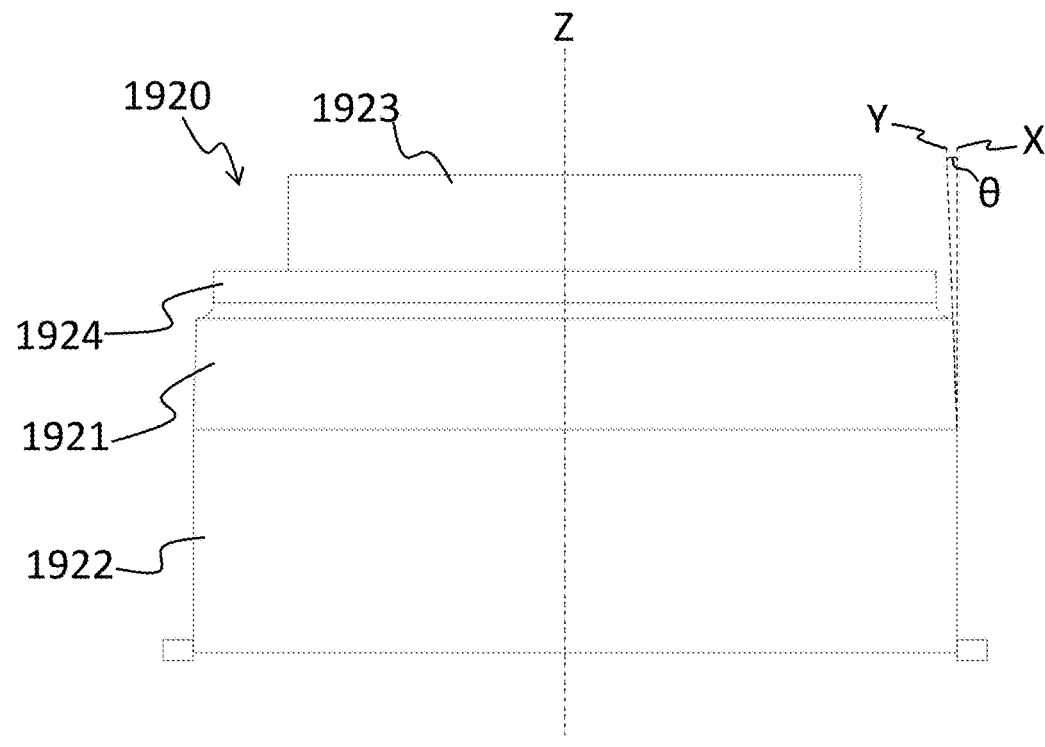
FIG. 21B shows a head 1920 of the holding jig 1900.

FIG. 21B shows the head 1920. The head 1920 has: a conical base 1921 with a bottom surface and a top surface; a cylindrical base 1922 extending from the bottom surface and having the same diameter as the bottom surface; a cylinder tip 1923 protruding from the top surface and having a diameter smaller than the diameter of the top surface; and a annular protrusion 1924 protruding from the top surface and having an outer diameter smaller than the diameter of the top surface and an inner diameter larger than the diameter of the cylinder tip. Auxiliary line X is parallel to the central axis Z of the head 1920 and extends along a side wall of the cylindrical base 1922. Auxiliary line Y extends along a side wall of the conical base 1921. The conical base 1921 has a conical trapezoidal shape having a diameter decreasing from its bottom surface to its top surface, so that the angle θ is between the auxiliary line X and the auxiliary line Y. In other words, the top surface is parallel to the bottom surface and area of the top surface is smaller than that of the bottom surface. The angle θ is, for example, 5±1° C., and is not limited to these values. The center of the top surface is located on a line extending perpendicular to the center of the bottom surface. The diameter of the cylindrical tip 1923 is smaller than the diameter of the opening part 1020 of the base part 1010. The diameter of the head 1920 is generally identical to the diameter of the through hole 1301 in the straight body 1300. The central axis of the conical base 1921, the central axis of the cylindrical base 1922, the central axis of the cylindrical tip 1923, and the central axis of the annular protrusion 1924 is preferably on the same line. The cylindrical tip 1923 protrudes more than the annular protrusion 1924. The protruding plates 1911 are not required, but the holding jig 1900 have preferably two protruding plates 1911 so that the holding jig 1900 can be easily removed from the holder 1030.

The holding jig 1900 may be made of glass, metal, elastic material (e.g., silicone rubber and plastic), or a combination thereof, but in order to increase the heating and cooling efficiency of the medical device 1001 (especially the biological sample 500 in the medical device 1001), a material with high thermal conductivity (e.g. metal such as silicon, aluminum or stainless steel) is preferred.

Figure 22:
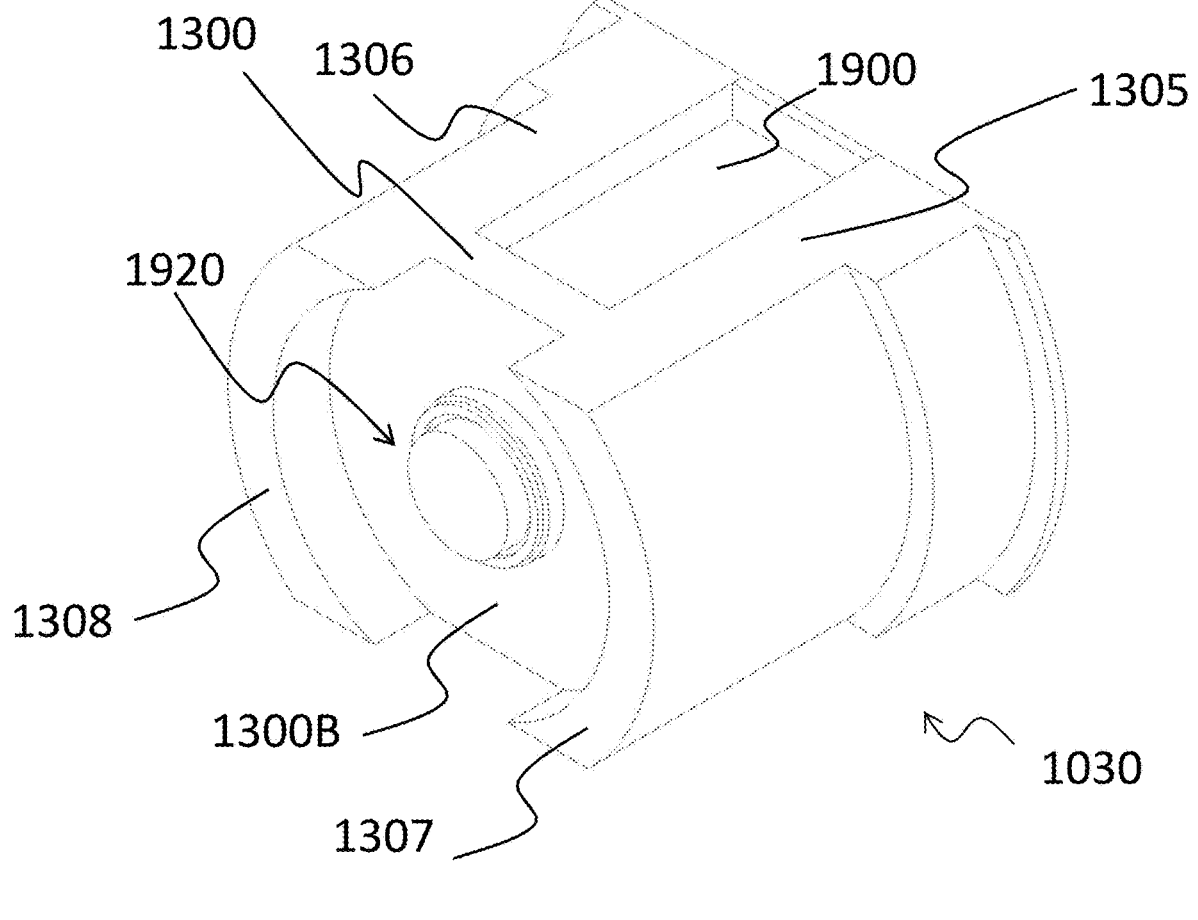
FIG. 22 shows the holder 1030 with the holding jig 1900 attached.
Figure 23:
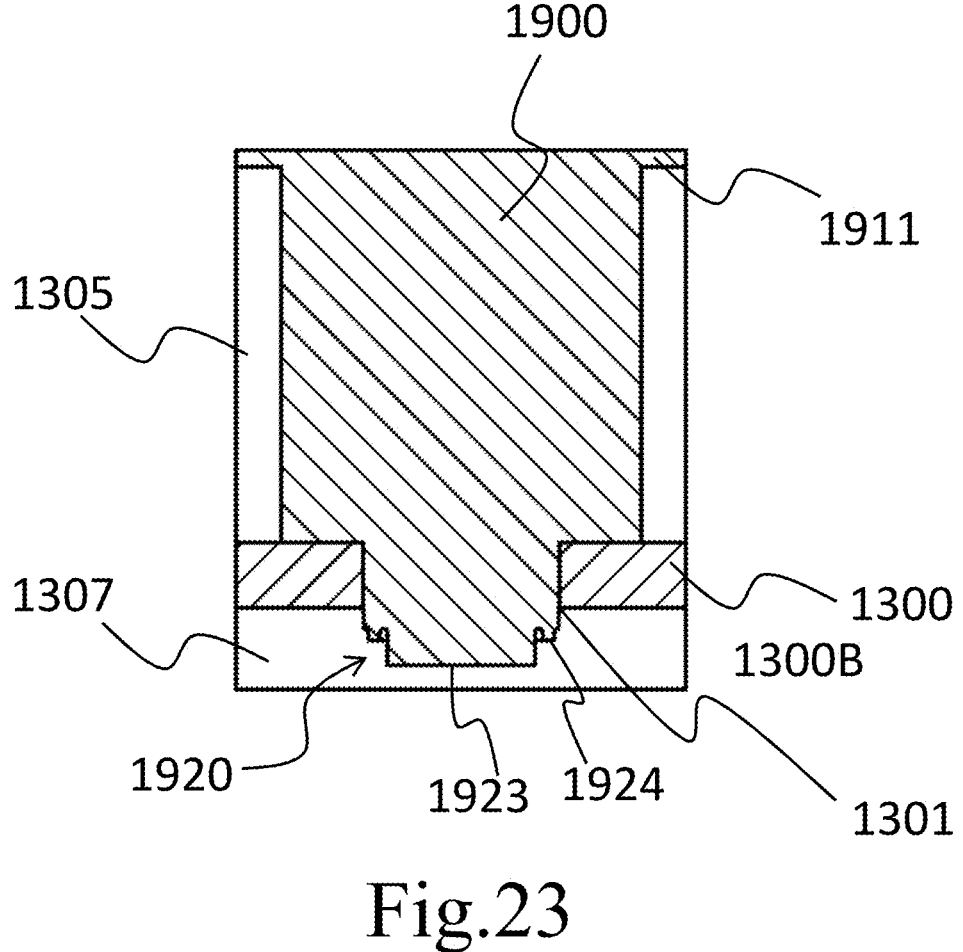
FIG. 23 shows a cross-sectional view of the holder 1030 with the holding jig 1900 attached, which is cut between the first arm 1305 and the second arm 1306 so as to pass through the central axis of the head 1920.

FIG. 22 shows the holder 1030 with the holding jig 1900 attached. FIG. 23 shows a cross-sectional view of the holder 1030 with the holding jig 1900 attached, which is cut between the first arm 1305 and the second arm 1306 so as to pass through the central axis of the head 1920. The cross-sectional view shown in FIG. 23 shows the first arm 1305 and the first leg 1307 at the back of the holding jig 1900. The holding jig 1900 is inserted between the first arm 1305 and the second arm 1306 in the direction of the straight body 1300 so that the head 1920 of the holding jig 1900 is inserted into the through hole 1301 of the straight body 1300.

The body 1910 of the holding jig 1900 according to this embodiment has rectangular shape, but may have other shapes. For example, the shape of the body of the holding jig suitable for the holders 30, 30A and 30B is a cylinder suitable for the shape of the respective through holes 301, 301A and 301B. In other words, the holding jig needs to have a size that can be inserted into the through hole of the holder and have at least the head and the body. The head and the body may be integrated as a single piece.

The thickness of the holding jig 1900 is preferably same as or slightly less than the distance between the first arm 1305 and the second arm 1306. The height of the holding jig 1900 may be the same as, higher than, or lower than the height of the first arm 1305 and the second arm 1306. The width of the holding jig 1900 can be any size that can be selected as long as it can be accommodated in the well 401 of the culture dish 400. A portion of the head 1920, particularly the cylindrical tip 1923 and the annular protrusion 1924, pass through the through hole 1301 in the straight body 1300 and protrude from the back surface 1300B of the straight body 1300.

Figure 24:
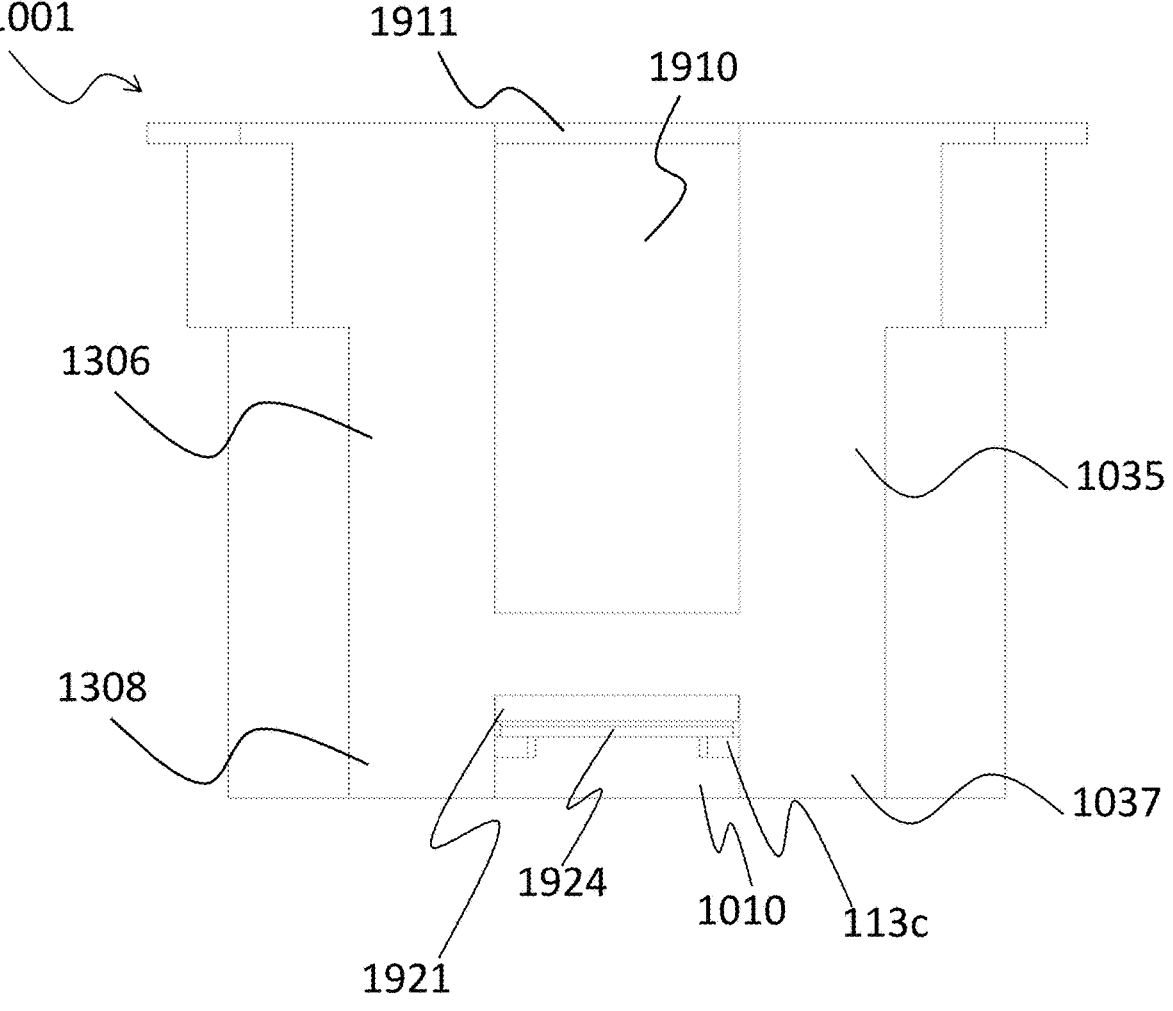
FIG. 24 shows the holder 1030 with the holding jig 1900 and a base part 1010 attached.
Figure 25:
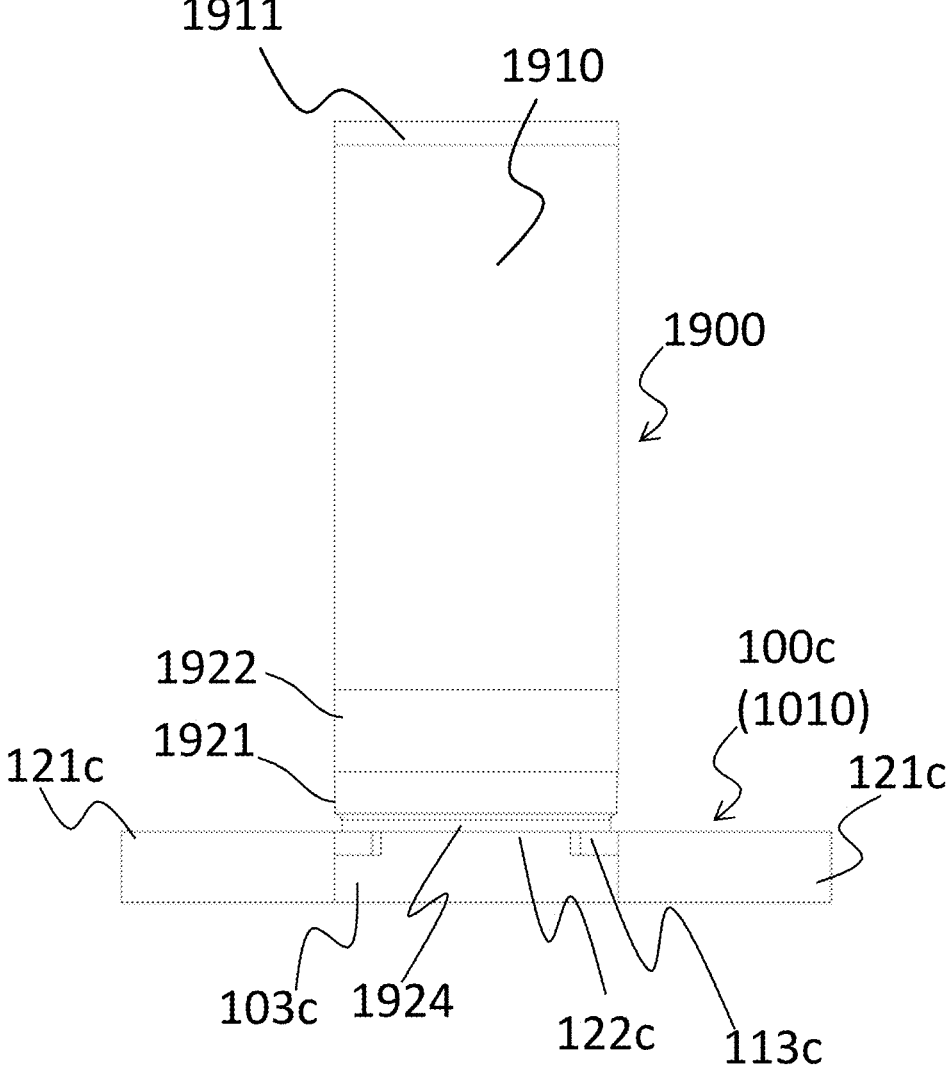
FIG. 25 shows the holding jig 1900 in contact with the base part 1010.
Figure 26:
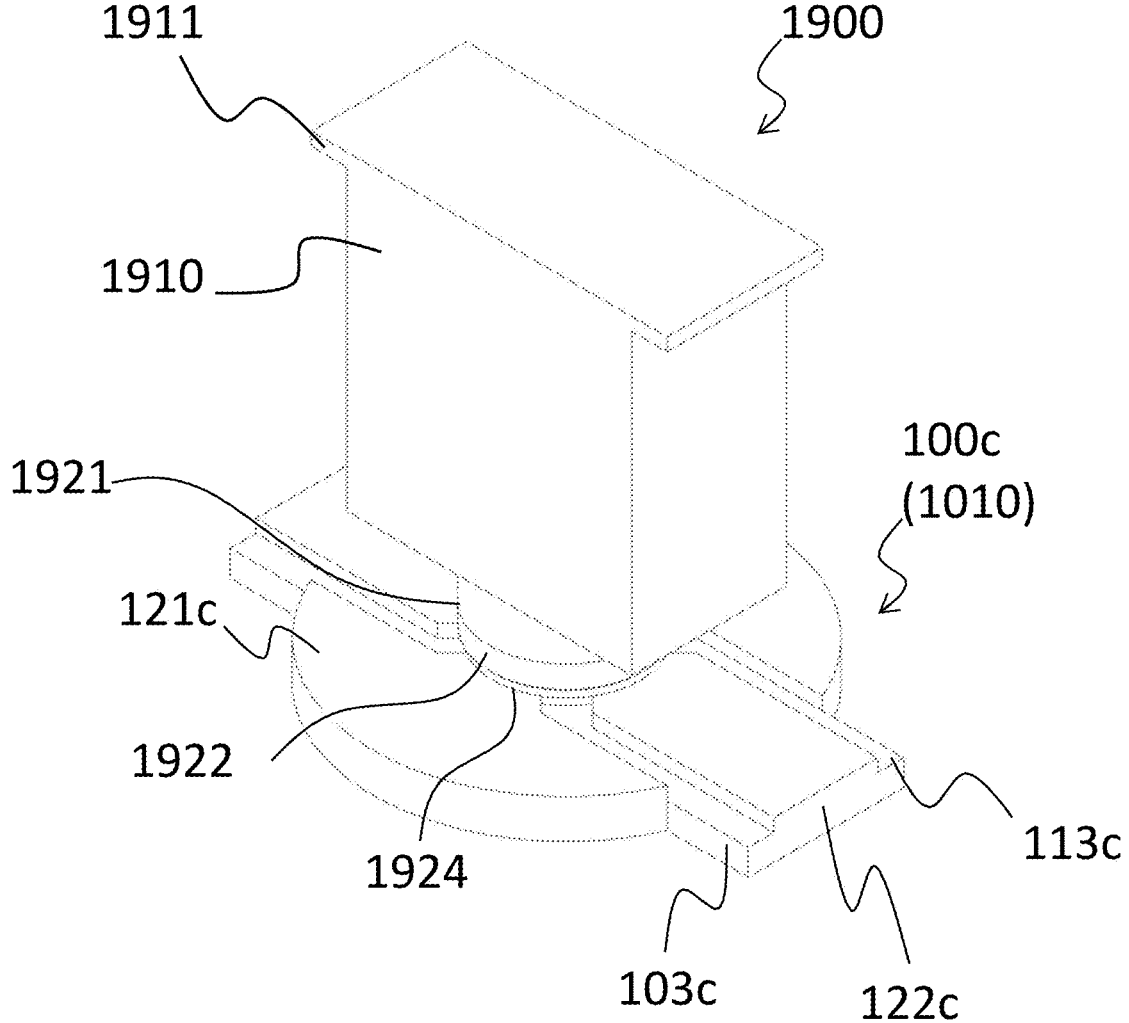
FIG. 26 shows the holding jig 1900 in contact with the base part 1010, based on a different viewpoint from the viewpoint of FIG. 25.
Figure 27:
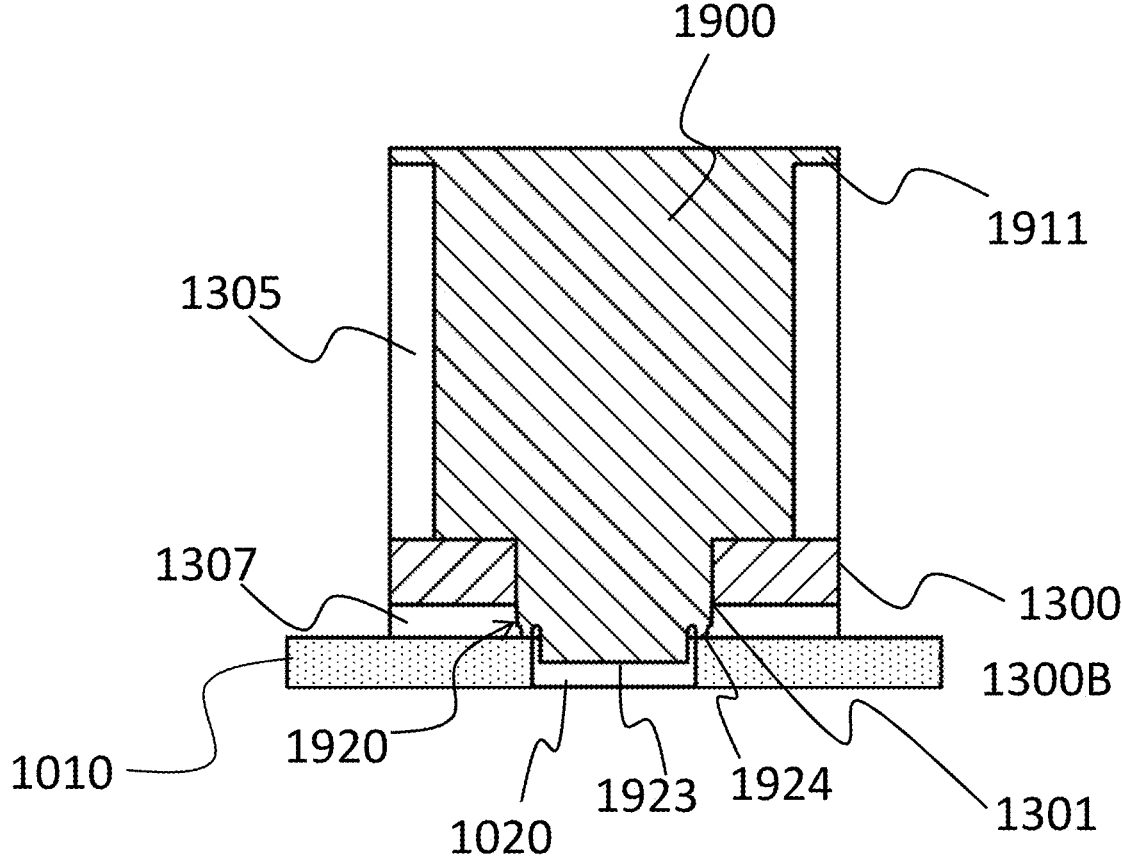
FIG. 27 shows a cross-sectional view of the holder 1030 with holding jig 1900 and base part 1010 attached.

FIG. 24 shows the holder 1030 with the holding jig 1900 and base part 1010 attached. Each of FIGS. 25 and 26 shows the holding jig 1900 in contact with the base part 1010. The holder 1030 is omitted in FIGS. 25 and 26 to clearly show the relationship between the holding jig 1900 and the base part 1010. FIG. 27 shows a cross-sectional view of the holder 1030 with the holding jig 1900 and the base part 1010 attached. The base part 1010 is provided between the first leg 1307 and the second leg 1308 so that the convex portion 120c faces the back surface 1300B of the base part 1010. The annular protrusion 1924 of the head 1920 is in contact with the convex portion 120c. The cylindrical tip 1923 of the head 1920 is partially inserted into the opening part 1020 of the base part 1010.

The embedding material 700 present in the culture compartment defined by the culture dish 400 and opening part 1020 is inserted into the opening part 1020 by the cylindrical tip 1923 of the head 1920, and excess embedding material 700 is ejected through the grooves of the base part 1010. The embedding material 700 that is not located near the grooves of the base part 1010 is moved into the grooves of the base part 1010 through an annular groove defined between the cylindrical tip 1923 and the annular protrusion 1924. Although the annular protrusion 1924 is not required, it is preferred that the head 1920 has the annular protrusion 1924 for quick and efficient ejection of the embedding material 700. By using the holding jig 1900, the embedding material

700 can be ejected efficiently and quickly, making the embedded biological sample 500 thinner. The amount of embedment material 700 ejected can be changed by the diameter of the cylindrical tip 1923 and the protruding length of the cylindrical tip 1923 from the annular protrusion 1924.

Holding Jig 1900A

Figure 28:
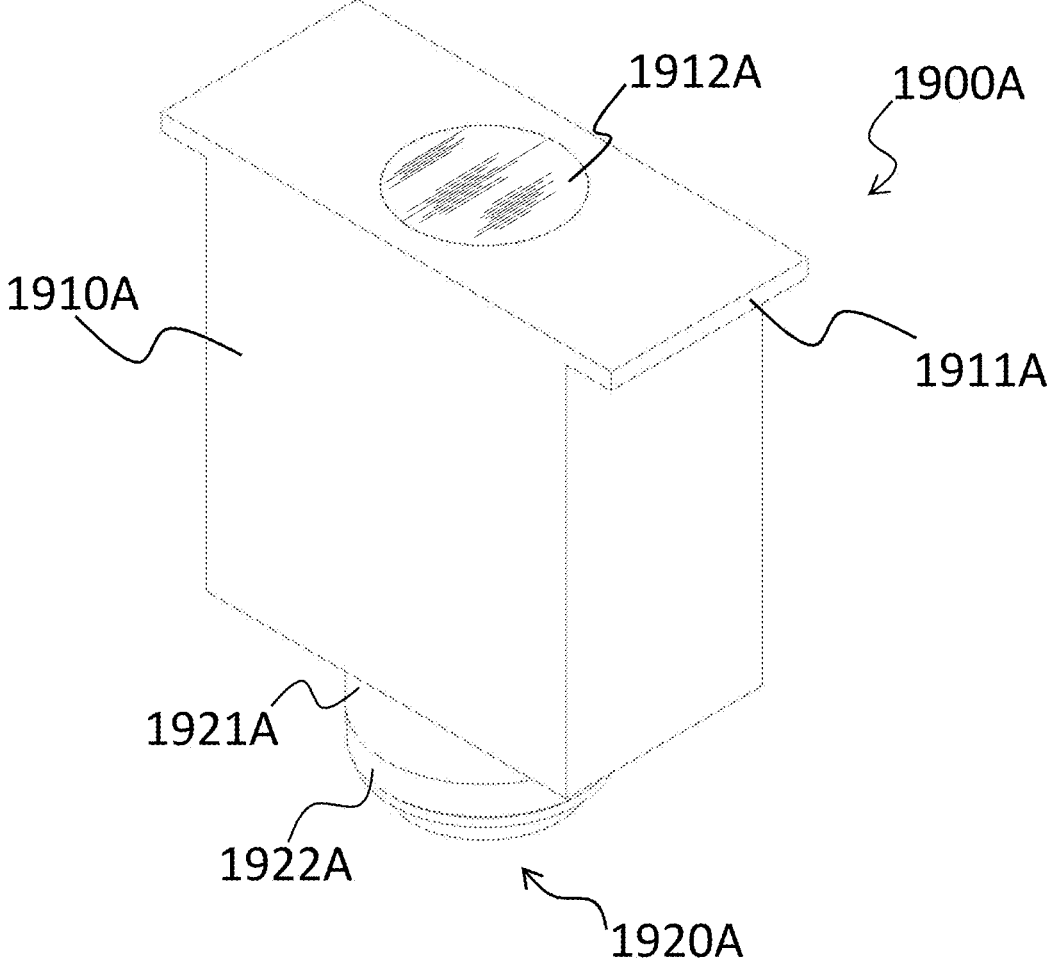
FIG. 28 shows another embodiment of a holding jig 1900A.
Figure 29:
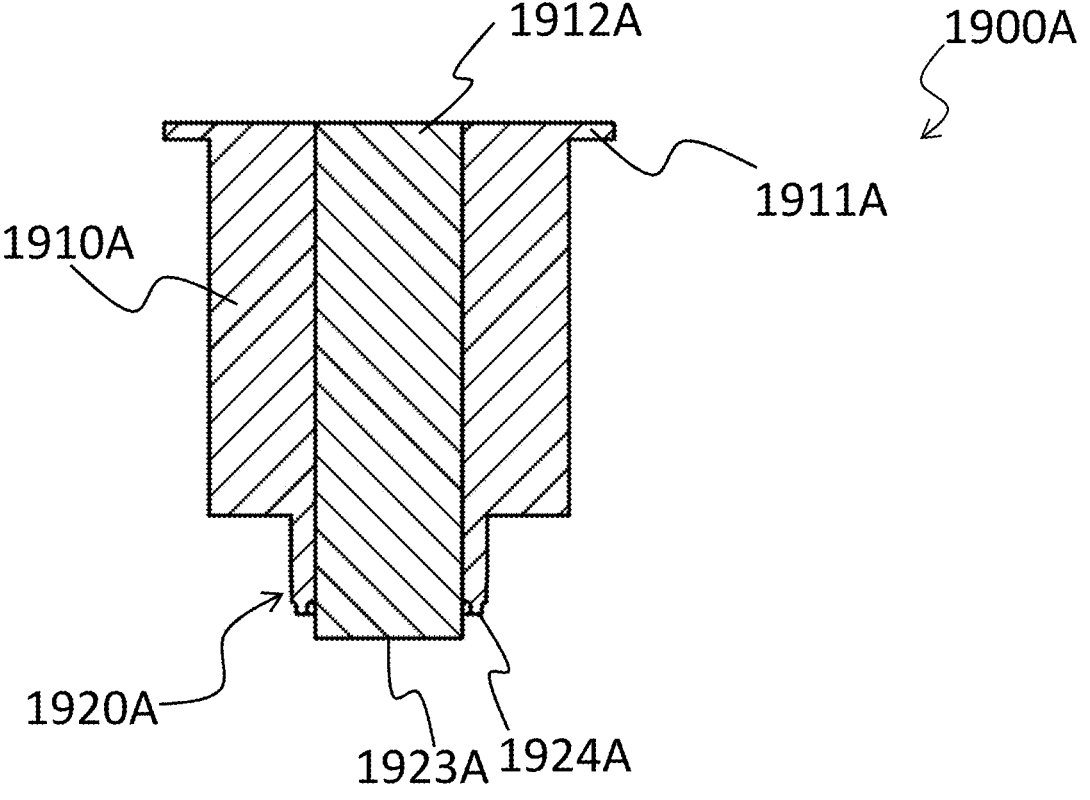
FIG. 29 shows a cross-sectional view of the holding jig 1900A.

FIG. 28 shows a holding jig 1900A according to further embodiments. The portion representing parallel thin lines indicates a transparent material. FIG. 29 shows a cross-sectional view of the holding jig 1900A. In the following, only the differences between the holding jig 1900 and the holding jig 1900A are shown.

The holding jig 1900A has: a body 1910A; a head 1920A protruding from one end of the body 1910A; two protruding plates 1911A, each protruding plate 1911A extending from the other end of the body 1910A orthogonal to the central axis of the head 1920A and in a direction away from the central axis; and a transparent body 1912A present along the central axis of the head 1920A so as to penetrate the body 1910A. The transparent body 1912A serves as the cylindrical tip 1923A of the head 1920A, but may also serve as part of the cylindrical tip 1923A. The embedding material 700 and the biological sample 500 in the culture compartment defined by the culture dish 400 and opening part 1020 can be directly observed through the transparent body 1912A. The transparent body 1912A in this embodiment has a cylindrical shape, but may have other shapes (e.g., a square cylinder). Its interior may be hollow. The transparent body 1912A may be made of any transparent material, for example, glass, plastic, acrylic glass, and polycarbonate.

Culturing and Embedding Method

A culturing and embedding method according to this embodiment has a step of setting the base part 1010 and the holder 1030 in the culture dish 400, a step of culturing the biological sample 500 in the opening part 1020, a step of embedding the biological sample 500 cultured in the opening part 1020 with the embedding material 700, a step of ejecting excess embedding material 700 by inserting the holding jig 1900 into the holder 1030, and a step of removing the biological sample 500. The culturing and embedding method according to this embodiment enables the excess embedding material 700 to be ejected, and the embedded biological sample 500 to be made thinner.

Kit

A kit includes the medical device 1 or 1001. The kit may include the single medical device 1 or 1001, or may include the multiple medical devices 1 or 1001. The kit may include the culture dish 400.

DESCRIPTION OF THE REFERENCE
NUMERAL

1, 10001 Medical device
10, 1010 Base part
20, 1020 Opening part
30, 30A, 30B, 30C, 1030 Holder
100, 100a, 100b, 100c Spacer support
101, 101a, 101b, 101c First opening part
102c Circular spacer support
103c Rectangular spacer support
110, 110a, 110b, 110c Groove
111c First groove
112c Second groove
113c Partial groove
114c Bend
120, 120a, 120b, 120c Convex portion 121*c* First convex portion
122*c* Second convex portion
130, 130*a*, 130*b*, 130*c* Inlet
140, 140*a*, 140*b*, 140*c* Outlet
150 Flow path
160*b* Notch
200 Spacer
201 Second opening part
300, 300A, 300B, 300C, 300D, 1300 Straight body
301, 301A, 301B, 301C, 301D, 1301 Through hole
302, 1302 Recess
303A Circular plate
304B Protruding portion
305C, 305D, 1305 First arm
306C, 306D, 1306 Second arm
310D, 1310 First arcuate side wall
320D, 1320 Second arcuate sidewall
330D, 1330 Flat side wall
340D, 1340 Overhang
400 Culture dish
401 Well of culture dish
500 Biological sample
600 Culture medium
700 Embedding material
800 Culture compartment
1300A Surface
1300B Back side
1307 First leg
1308 Second leg
1900, 1900A Holding jig
1910, 1910A Body
1911, 1911A Protrusion plate
1912A Transparent body
1920, 1920A Head
1921, 1921A Conical base 1922, 1922A Cylindrical base
1923, 1923A Cylindrical tip
1924, 1924A Annular protrusion

I claim:

1. A medical device for culturing a biological sample and embedding the biological sample with an encapsulation material, comprising:
   a base part with an opening part and at least one groove;
   a holder for holding the base part to a culture dish; and
   a spacer for covering the at least one groove,
   wherein,
   the at least one groove has an inlet and an outlet,
   the at least one groove is in fluid communication with the opening part via the inlet and in fluid communication with outside of the opening part via the outlet, and
   a channel in fluid communication with the opening part is defined by the at least one groove covered by the spacer.

2. The medical device according to claim 1, wherein the holder has a straight body with a through hole and a recess for accommodating at least a part of the base part at one of ends of the straight body, and
   the through hole is in fluid communication with the opening part.

3. The medical device according to claim 2, further comprising a holding jig having a size capable of being inserted into the through hole, wherein the holding jig has a head and a body.

4. The medical device according to claim 1, wherein the at least one groove is at least two grooves.

5. The medical device according to claim 1, wherein the spacer is made of an elastic material.

6. A kit comprising the medical device according to claim 1.

\* \* \* \* \*